United States Patent [19]

Morton, Jr.

[11] 4,181,798
[45] Jan. 1, 1980

[54] METHYLENECYCLOPENTANE DERIVATIVES

[75] Inventor: Douglas R. Morton, Jr., Portage, Mich.

[73] Assignee: The Upjohn Company, Kalamazoo, Mich.

[21] Appl. No.: 947,688

[22] Filed: Oct. 2, 1978

Related U.S. Application Data

[63] Continuation-in-part of Ser. No. 764,332, Jan. 31, 1977, abandoned, which is a continuation-in-part of Ser. No. 691,792, Jun. 1, 1976, abandoned.

[51] Int. Cl.² .................................................. C07D 407/08
[52] U.S. Cl. ..................................... 542/426; 568/838
[58] Field of Search ......................... 568/838; 542/426

[56] References Cited

U.S. PATENT DOCUMENTS

| | | | |
|---|---|---|---|
| 3,867,375 | 2/1975 | Alvarez et al. | 542/426 |
| 3,980,642 | 9/1976 | Hess et al. | 542/426 |
| 3,987,087 | 10/1976 | Bundy | 542/426 |

OTHER PUBLICATIONS

Stork et al., J.A.C.S. 98 (6747).
Stork et al., J.A.C.S. 97 (1975) pp. 4745–4746, pp. 6260–6261.

*Primary Examiner*—Arthur P. Demers
*Attorney, Agent, or Firm*—Morris L. Nielsen

[57] ABSTRACT

Methylenecyclopentane derivatives, for example

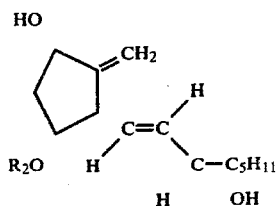

wherein $R_2$ is a blocking group such as tetrahydropyranyl, and a process for preparing them; said derivatives having utility as prostaglandin intermediates.

19 Claims, No Drawings

METHYLENECYCLOPENTANE DERIVATIVES

CROSS REFERENCE TO RELATED APPLICATIONS

This application is a continuation-in-part of copending application Ser. No. 764,332, filed Jan. 31, 1977, now abandoned, which was a continuation-in-part of then copending application Ser. No. 691,792 filed June 1, 1976 and since abandoned.

BACKGROUND OF THE INVENTION

This invention relates to intermediates useful in the preparation of prostaglandin analogs and to a process for preparing them.

Each of the known prostaglandins is a derivative of prostanoic acid which has the following structure and atom numbering:

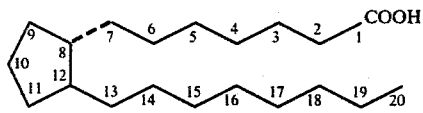

A systematic name for prostanoic acid is 7-[(2β-octyl)-cyclopent-1α-yl]heptanoic acid.

Prostaglandin $E_1$, "$PGE_1$", has the following structure:

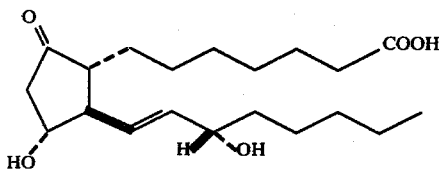

Prostaglandin $F_{1\alpha}$, "$PGF_{1\alpha}$", has the following structure:

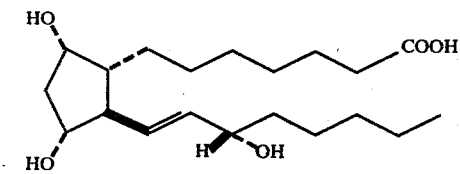

The prostaglandin formulas mentioned above each have several centers of asymmetry. Each formula represents a molecule of the particular optically active form of the prostaglandin obtained from certain mammalian tissues, for example, sheep vesicular glands, swine lung, and human seminal plasma. or by reduction or dehydration of a prostaglandin so obtained. See, for example, Bergstrom et al., Pharmacol. Rev. 20, 1 (1968), and references cited therein. The mirror image of each formula represents a molecule of the other enantiomeric form of that prostaglandin. The racemic form of the prostaglandins consists of equal numbers of two types of molecules, one represented by one of the above formulas and the other represented by the mirror image of that formula. Thus, both formulas are needed to define a racemic prostaglandin. See Nature 212. 38 (1966) for discussion of the stereochemistry of the prostaglandins.

In the formulas above, as well as in the formulas given hereinafter, broken line attachments to the cyclopentane ring indicate substituents in alpha configuration, i.e., below the plane of the cyclopentane ring. Heavy solid line attachments to the cyclopentane ring indicate substitutents in beta configuration, i.e., above the plane of the cyclopentane ring. In the formulas above. the hydroxyl attachment to carbon 15 is in the alpha configuration, as indicated by the broken line. In formulas below, this convention is also used for intermediates having hydroxyl substituted at the corresponding position on the side chain. A wavy line ∼ indicates attachment to the side chain in alpha or beta configuration.

The various optically active and racemic prostaglandins and their alkyl esters are useful for various pharmacological purposes. With particular regard to $PGF_{1\alpha}$, see, for example, Bergstrom et al., Pharmacol. Rev. 20, 1 ( 1968), and references cited therein. As to the other prostaglandins, see, for example, Ramwell et al., Nature 221, 1251 (1969).

A group of prostaglandin analogs having a divalent phenylene moiety in the carboxyl-terminated side chain of the prostanoic acid structure (I) was disclosed in a pending U.S. patent application by Norman A. Nelson, Ser. No. 604,158, filed Aug. 13, 1975.

Included among those phenylene prostaglandin analogs were compounds represented by the formulas:

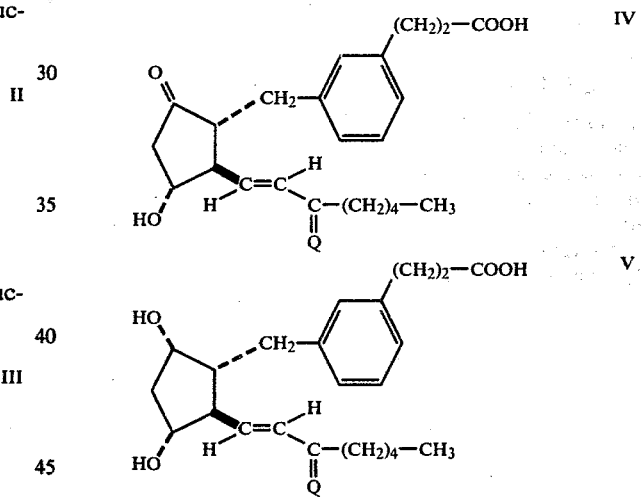

wherein Q is

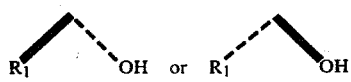

and $R_1$ is hydrogen or alkyl of one to 4 carbon atoms, inclusive. Previously, certain prostaglandin analogs having an oxa oxygen (—O—) and a divalent phenylene moiety

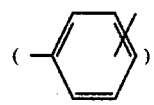

in the carboxyl-terminated side chain of the prostanoic acid structure (I) were disclosed. See U.S. Pat. No. 3,933,898.

Included among those phenylene-oxa prostaglandin analogs were compounds represented by the formulas:

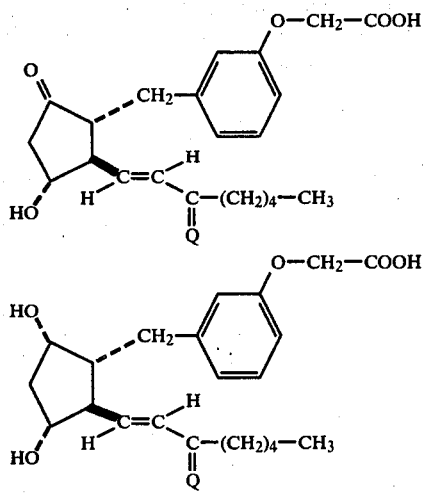 VI

VII where Q is as defined above.

Each of the phenylene and phenylene-oxa prostaglandin analogs is useful in place of the corresponding known prostaglandins for at least one of their known pharmacological purposes, which include reduction of gastric secretion, inhibition of blood platelet aggregation, increase of nasal patency, and labor inducement at term.

SUMMARY OF THE INVENTION

It is the purpose of this invention to provide intermediates useful in the preparation of phenylene and phenylene oxa prostaglandin analogs. It is a further purpose of provide novel processes for preparing these intermediates.

Accordingly, there are provided methylenecyclopentane derivatives of the formula

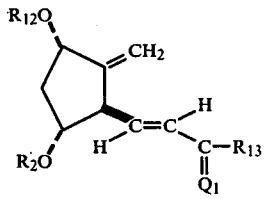 VIII wherein $Q_1$ is

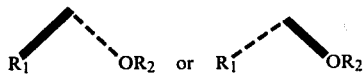

wherein $R_1$ is hydrogen or alkyl of one to 4 carbon atoms, inclusive; wherein $R_2$ is a blocking group including tetrahydropyranyl, tetrahydrofuranyl, 1-ethoxyethyl, or a group of the formula

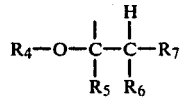

wherein $R_4$ is alkyl of one to 18 carbon atoms, inclusive, cycloalky of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_5$ and $R_6$ are the same or different, being hydrogen, alkyl of one to 4 carbon atoms, inclusive, phenyl or phenyl substituted with one, 2, or 3 alkyl of one to 4 carbon atoms, inclusive, or, when $R_5$ and $R_6$ are taken together, $-(CH_2)_a-$ or $-(CH_2)_b-O-(CH_2)_c-$ wherein a is 3, 4, or 5, b is one, 2, or 3, and c is one, 2 or 3 with the proviso that b plus c is 2, 3, or 4, and wherein $R_7$ is hydrogen or phenyl; wherein $R_{12}$ is (1) hydrogen; (2) silyl of the formula $-Si(A)_3$ wherein A is alkyl of one to 4 carbon atoms, inclusive, phenyl, phenyl substituted with one to 2 fluoro, chloro, or alkyl of one to 4 carbon atoms, inclusive, or aralkyl of 7 to 12 carbon atoms, inclusive, the A groups being the same or different; or (3) carboxyacyl of the formula

wherein $R_9$ is hydrogen, alkyl of one to 19 carbon atoms, inclusive, or aralkyl of 7 to 12 carbon atoms, inclusive, wherein alkyl or aralkyl are substituted with zero to 3 halo atoms; and wherein $R_{13}$ is

 (1)

or

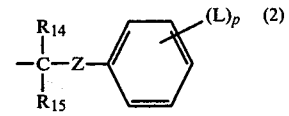 (2)

wherein $C_gH_{2g}$ is alkylene of one to 9 carbon atoms, inclusive, with one to 5 carbon atoms, inclusive, in the chain between $-CR_{14}R_{15}-$ and terminal methyl, wherein $R_{14}$ and $R_{15}$ are hydrogen, alkyl of one to 4 carbon atoms, inclusive, or fluoro, being the same or different, with the proviso that one of $R_{14}$ and $R_{15}$ is fluoro only when the other is hydrogen or fluoro and the further proviso that neither $R_{14}$ nor $R_{15}$ is fluoro when Z is oxa $(-O-)$; wherein Z represents an oxa atom $(-O-)$ or $C_jH_{2j}$ wherein $C_jH_{2j}$ is a valence bond or alkylene of one to 9 carbon atoms, inclusive, with one to 6 carbon atoms, inclusive, between $CR_{14}R_{15}-$ and the phenyl ring; and wherein L is alkyl of one to 4 carbon atoms, inclusive, fluoro, chloro, trifluoromethyl, or $-OR_{16}-$wherein $R_{16}$ is alkyl of one to 4 carbon atoms, inclusive, and p is zero, one, 2 or 3, with the proviso that not more than two L's are other than alkyl and when p is 2 or 3 the L's are either the same or different There are further provided substituted cyclopentanone derivatives of the formula

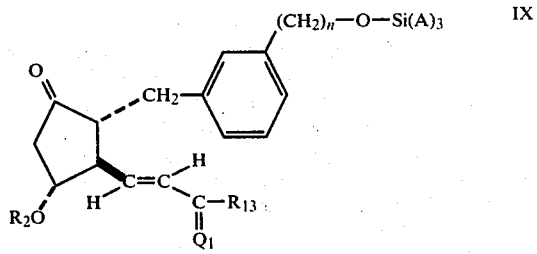 IX wherein A, $Q_1$, $R_2$ and $R_{13}$ are as defined above and wherein "n" is zero or 3, and a process for preparing those cyclopentanone derivatives by (a) oxidizing a compound of the formula

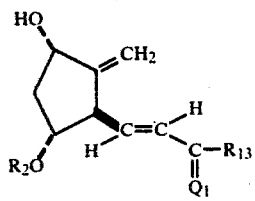

wherein $Q_1$, $R_2$, and $R_{13}$ are as defined above, to form an enone of the formula

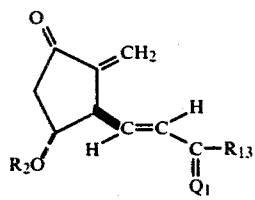

and (b) subjecting that enone to conjugative addition with a lithium diaryl cuprate reactant prepared from

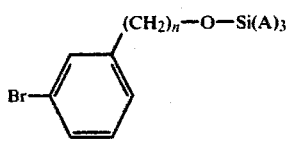

wherein A and "n" are as defined above.

With regard to formulas IV to XI, examples of alkyl of one to 4 carbon atoms, inclusive, are methyl, ethyl, propyl, butyl, and isomeric forms thereof. Examples of alkyl of one to 18 carbon atoms, inclusive, are those given above, and pentyl, hexyl, heptyl, octyl, nonyl, decyl, undecyl, dodecyl, tridecyl, tetradecyl, pentadecyl, hexadecyl, octadecyl and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are (o-, m-, or p-)chlorophenyl, 2,4-dichlorophenyl, 2,4,6-trichlorophenyl, (o-, m-, or p-)tolyl, p-ethylphenyl, p-tert-butylphenyl, 2,5-dimethylphenyl, 4-chloro-2-methylphenyl, and 2,4-dichloro-3-methylphenyl.

Examples of alkylene of to 9 carbon atoms, inclusive, with one to 5 carbon atoms, inclusive, in the chain, within the scope of $C_gH_{2g}$ as defined above, are methylene, ethylene, trimethylene, tetramethylene, and pentamethylene, and those alkylene with one or more alkyl substituents on one or more carbon atoms thereof, e.g. —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_2$—C(CH$_3$)$_2$—, —CH$_2$—CH(CH$_3$)—CH$_3$—, —CH$_2$—CH$_2$—CH(CH$_2$CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$, and —CH$_2$—CH$_2$—CH$_2$—CH$_2$—CH(CH$_3$)—. Examples of alkylene of one to 9 carbon atoms, inclusive, substituted with zero, one, or 2 fluoro, with one to 6 carbon atoms in he chain, within the scope of $C_jH_{2j}$ as defined above, are those given above for $C_gH_{2g}$ and hexamethylene, including hexamethylene with one or more alkyl substituents on one or more carbon atoms thereof, and including those alkylene groups with one or 2 fluoro substituents on one or 2 carbon atoms thereof, e.g. —CHF—CH$_2$—, —CHF—CHF—, —CH$_2$—CH$_2$—CF$_2$—, —CH$_2$—CHF—CH$_2$—, —CH$_2$—CH$_2$—CF(CH$_3$)—, —CH$_2$—CH$_2$—CF$_2$—CH$_2$—, —CH(CH$_3$)—CH$_2$—CH$_2$—CHF—, —CH$_2$—CH$_2$—CH$_2$—CH$_2$—CF$_2$—, —CHF—CH$_2$—CH$_2$—CH$_2$—CHF—, —CF$_2$—CH$_2$—CH$_2$—CH$_2$—CH$_2$—, —CH$_2$—CH$_2$—CH$_2$—CF$_2$—CH$_2$—CH$_2$—, and —CH$_2$—CH$_2$—CH$_2$—CH$_2$—CH$_2$—CF$_2$.

Examples of

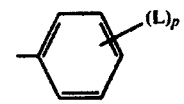

as defined above are
phenyl,
(o-, m-, or p-)tolyl,
(o-, m-, or p-)ethylphenyl,
(o-, m-, or p-)propylphenyl,
(o-, m-, or p-)butylphenyl,
(o-, m-, or p-)isobutylphenyl,
(o-, m-, or p-)tert-butylphenyl,
2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
2-propyl-(o-, m-, or p-) tolyl,
4-butyl-m-tolyl,
6-tert-butyl-m-tolyl,
4-isopropyl-2,6-xylyl,
3-propyl-4-ethylphenyl,
(2,3,4-, 2,3,5-, 2,3,6-, or 2,4,5-)trimethylphenyl,
(o-, m-, or p-)fluorophenyl,
2-fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-, 4-, 5, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-, 3,4-, or 3,5-)dichlorophenyl,
4-chloro-3-fluorophenyl,
(3-, or 4-)chloro-2-fluorophenyl,
α,α,α-trifluoro-(o-, m-, or p-)tolyl,
(o-, m-, or p-)methoxyphenyl,
(o-, m-, or p-)ethoxyphenyl, (4- or 5-)chloro-2-methoxyphenyl, and 2,4-dichloro(5- or 6-)methoxphenyl.

Reference to Charts A, B, and C, herein, will make clear the steps by which the above novel intermediates are prepared and utilized in preparing the phenylene and phenylene-oxa prostaglandin analogs.

In Chart A, steps to the formula-X and -XI compounds are shown, together with steps leading to phenylene products of formula Iv. In Chart A, the terms, A, Q, $Q_1$, and $R_2$ are as defined above.

The bicyclic lactone starting reactants of formula XII are known in the art or are available by processes known in the art. For example, when $R_{13}$ is $-(CH_2)_4-CH_3$, and Q is

see Corey et al., J. Am. Chem. Soc. 92, 397 (1970). For other XII lactones see, for example, U.S. Pat. Nos. 3,903,131, 3,967,293, 3,987,087, and British specification cited in Derwent Farmdoc No. 73279U. See especially U.S. Pat. No. 3,931,279 issued to N.A. Nelson, particularly columns 27-34, which are incorporated herein by reference.

In step (a) of Chart A, the formula-XIII blocked lactones are formed reactants XII by methods described herein or known in the art.

CHART A

XII step (a)

XIII step (b)

step (c)

CHART A —continued

XV

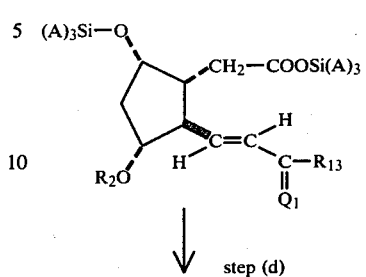

step (d)

XVI

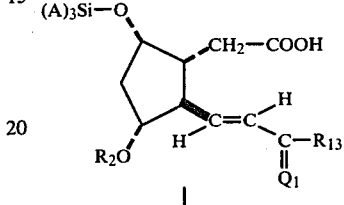

step (e)

XVII

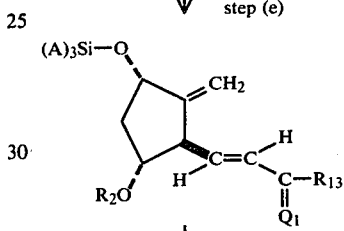

step (f)

X

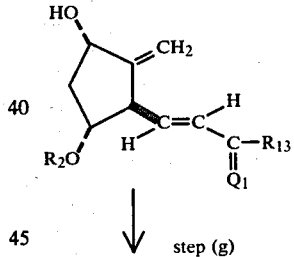

step (g)

XI

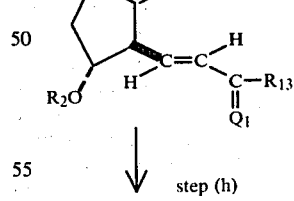

step (h)

XVIII

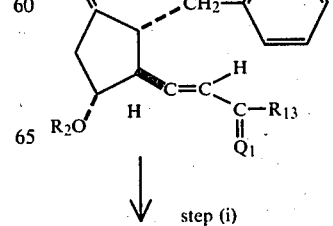

step (i)

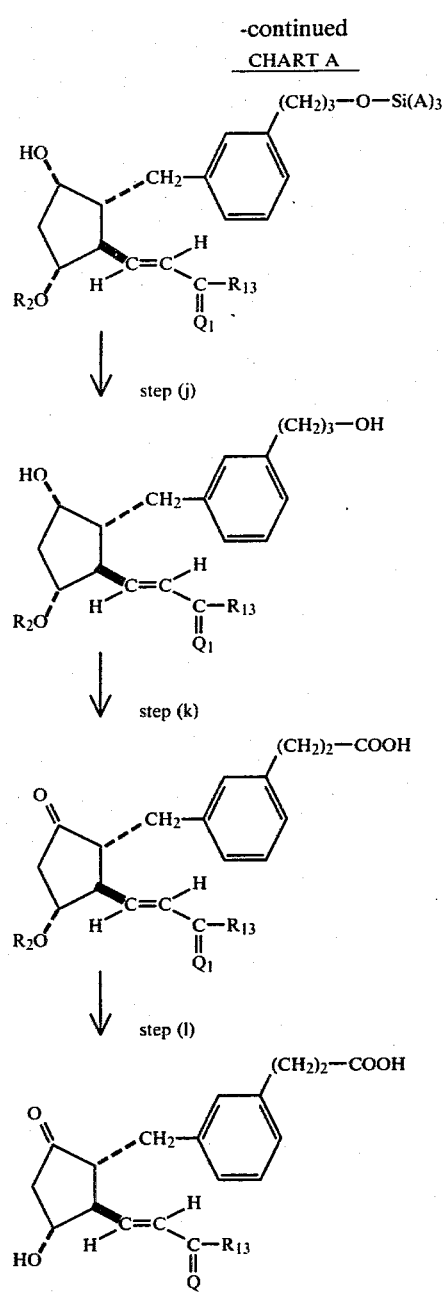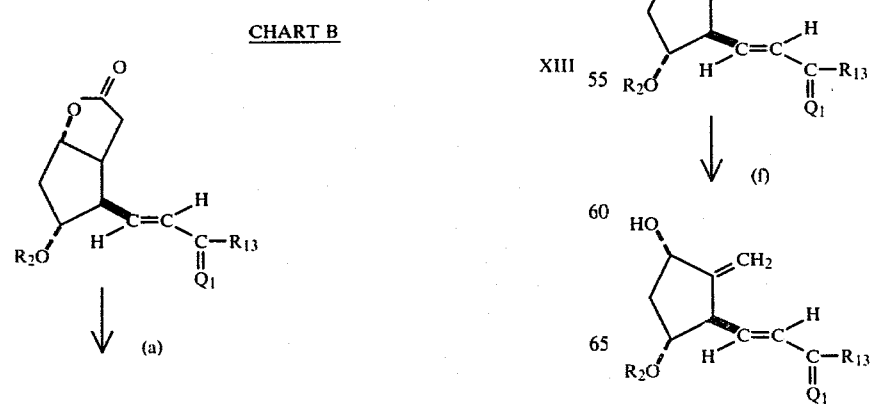

CHART C
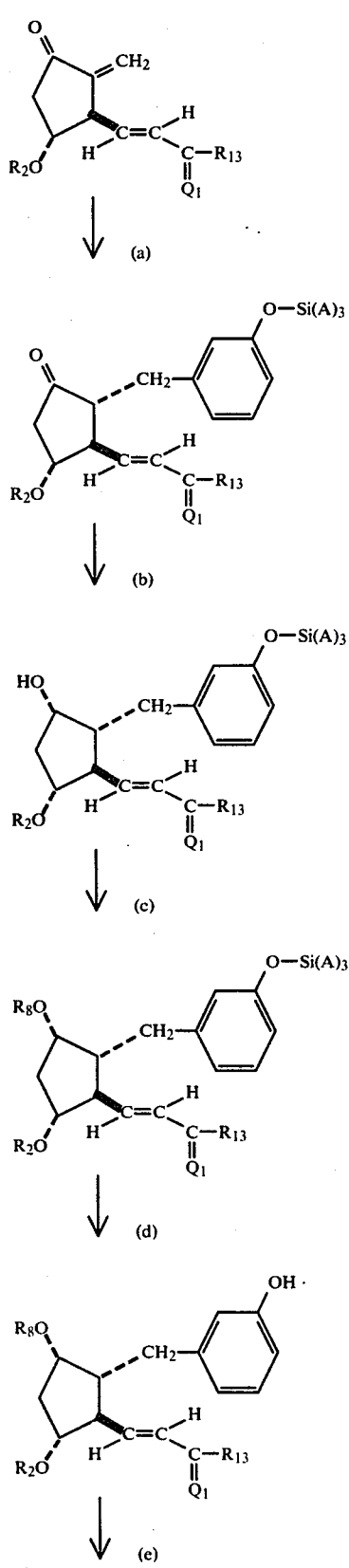
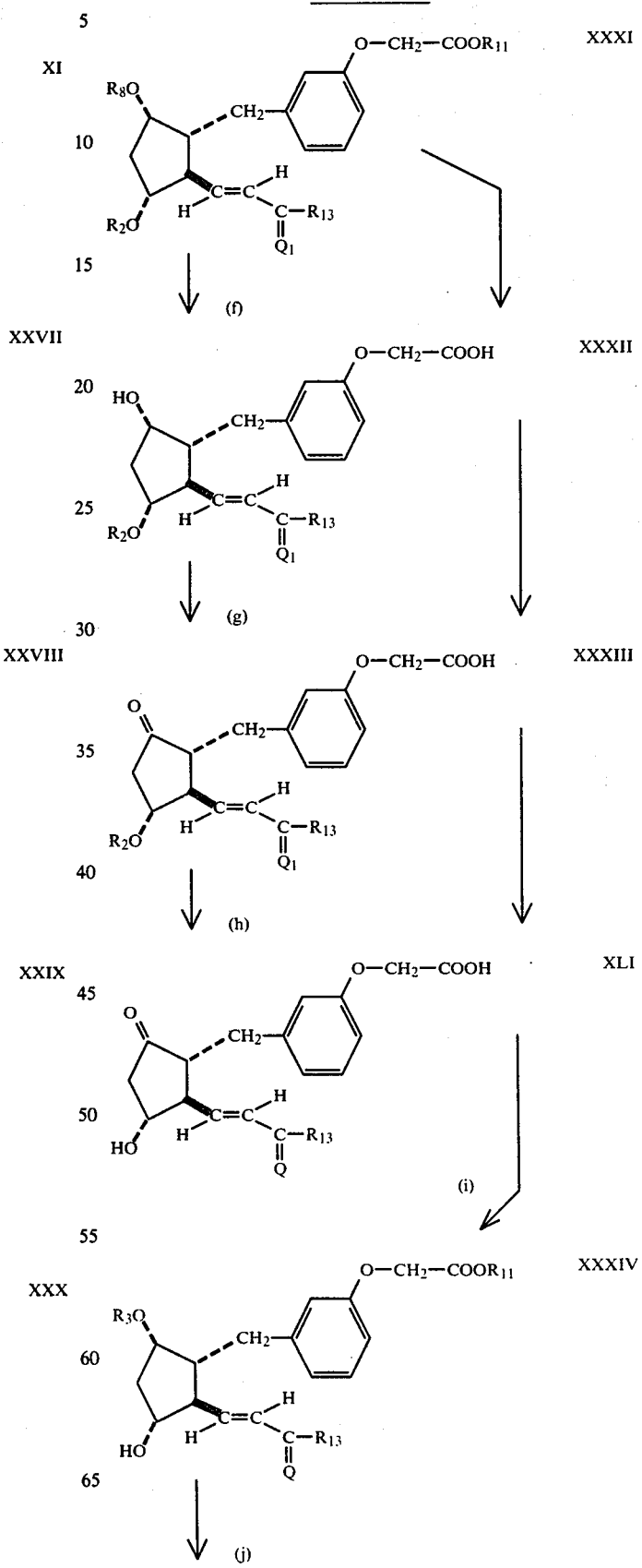

-continued
CHART C

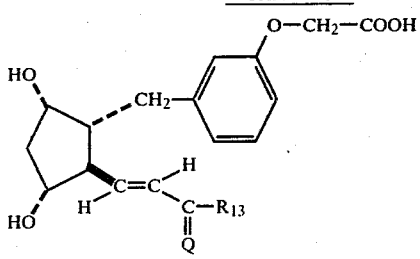

XLII

When the blocking group $R_2$ is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When the blocking group is of the formula

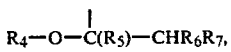

as defined above, the appropriate reagent is a vinyl ether, e.g. isobutyl vinyl ether or any vinyl ether of the formula $R_4$—O—$C(R_5)$=$CR_6R_7$ wherein $R_4$, $R_5$, $R_6$, and $R_7$ are as defined above; or an unsaturated cyclic or heterocyclic compound, e.g. 1-cyclohex-1-yl methyl ether

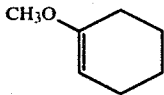

or 5,6-dihydro-4-methoxy-2H-pyran

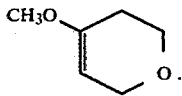

See C. B. Reese et al., J. Am. Chem. Soc. 89, 3366 (1967). The reaction conditions for such vinyl ethers and unsaturates are similar to those for dihydropyran above.

In step (b) the triol acid of formula-XIV is formed by hydrolysis, opening the lactone ring. The hydrolysis occurs in a solvent containing water, for example, in methanol, dioxane, or tetrahydrofuran, in the presence of a base, such as an alkali metal hydroxide or carbonate, preferably sodium hydroxide. The reaction occurs in the range of about 0° to 100° C. and is conveniently done at ambient conditions. In this, as in all steps described herein, the duration of the reaction is determined most readily by following it with TLC. During this step the blocking groups $R_2$ are not removed.

In step (c) silylated compound XV is obtained from XIV by procedures known in the art or described herein. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted monochlorosilanes suitable for this purpose include chlorotrimethylsilane, chlorotriisobutylsilane, tert-butyldimethylchlorosilane, chlorotriphenylsilane, chlorotris(p-chlorophenyl)silane, chlorotri-m-tolylsilane, and tribenzylchlorosilane. Alternately, a chlorosilane is used with a corresponding disilazane. Examples of other silylating agents include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

Although a wide variety of silylating agents are available, it is preferred that the silyl groups on the ring contain at least one hindered group: for example isopropyl, secondary butyl, tert-butyl, cyclohexyl, or phenyl. The silyl groups with hindered substituents are characterized as being less susceptible to hydrolysis than, for example, trimethylsilyl, and therefore resistent to replacement during subsequent steps, particularly step (e). Examples of preferred silyl groups for the cyclopentane ring are:

isopropyldimethylsilyl,
sec-butyldimethylsilyl,
tert-butyldimethylsilyl,
triisopropylsilyl,
cyclohexyldimethylsilyl,
and triphenylsilyl.

In addition to the silylation methods discussed above, it is advantageous to silylate with a chlorosilane in the presence of imidazole in a solvent such as dimethylformamide. See Corey et al., J. Am. Chem. Soc. 94, 6190 (1972). The temperature range for the reaction is about −10° to +80° C.

In step (d) the formula-XVI compound is obtained by selective hydrolysis of silyl from the terminal carboxyl group. Generally an alkali metal carbonate is employed in water and a cosolvent such as methanol, tetrahydrofuran or dioxane, in a temperature range of about −10° to +100° C. If the silyl group on the ring is hindered, a stronger base such as sodium hydroxide may be used to selectively remove the silyl group from the carboxyl.

In step (e), oxidative decarboxylation is employed to yield the formula-XVII compound. See J. D. Bacha and J. K. Kochi, Tetrahedron, 24, 2215 (1968). Compound XVI is treated in solution, for example in benzene, toluene, xylene, or heptane, with a copper (II) salt such as the acetate, chloride, or nitrate, solubilized with a compound such as pyridine, followed by a lead (IV) salt such as the acetate or benzoate. Decarboxylation may be done either thermally (60°–100° C.) or photochemically using radiation of about 3000–3700 Å as from mercury vapor lamps, in a temperature range of about 0° to 60° C.

In step (f), the compound of formula X is obtained by selective hydrolysis of the silyl groups without removing the $R_2$ blocking groups. For this purpose a base is used in a liquid medium such as dioxane or tetrahydrofuran. For unhindered silyl groups an alkali metal carbonate is useful; for hindered groups, such as tert-butyldimethylsilyl, a tetra-n-alkylammonium fluoride such as tetra-n-butylammonium fluoride is preferred, in a temperature range of −10° to +50° C.

In step (g) the formula-XI ketone is obtained by oxidation. Useful for this purpose is pyridinium chlorochromate, Collins reagent, and especially Jones reagent at about −40° C. to about 25° C.

In step (h) compound XVIII is obtained by conjugative addition with a lithium diaryl cuprate reactant prepared from

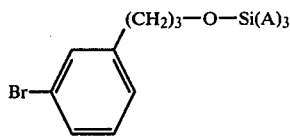

wherein $Si(A)_3$ is as defined above. For the synthesis of a cuprate reagent see, for example, Posner, Org. React. 19, 1 (1972) and Normant, Synthesis 63 (1972). See also Posner for typical conditions for addition to an enone. it is conveniently done in a solvent such as diethyl ether or tetrahydrofuran at about −78° C. to 0° C. A related addition has been reported by Stork et al., J. Am. Chem. Soc. 97, 4745 (1975); a non-aromatic cuprate reactant was used.

In step (i) compound XIX is obtained by reduction of the ketone, using methods known in the art, for example with sodium borohydride at about 0° C. or lithium tri(-sec-butyl)borohydride. Both $9\alpha$ and $9\beta$ hydroxy epimers may be formed in the reduction but is is not necessary to separate them for step (k).

In step (j) the terminal silyl group is removed to form compound XX, using methods described above, for example hydrolysis with tetra-n-butylammonium fluoride for tert-butyldimethylsilyl groups.

In step (k) compound XXI is obtained by oxidation, using for example the Jones reagent.

Finally, in step (l) of Chart A and $R_2$ blocking groups are removed by mild acid hydrolysis as known in the art, yielding final acid compound XL.

Chart B shows an alternate route of synthesis of the formula-X methylene compound starting with the formula-XIII lactone of Chart A. In Chart B the terms $Q_1$, $R_2$ and $R_{13}$ have the same meaning as in Chart A; $R_8$ represents (1) carboxyacyl including, for example, formyl, acetyl, pivaloyl, and the like, or (2) an aromatic acyl group such as benzoyl or substituted benzoyl, nonesterified phthaloyl, naphthoyl, or substituted naphthoyl. Carboxyacyl is represented by the formula

wherein $R_9$ is hydrogen, alkyl of one to 19 carbon atoms, inclusive, or aralkyl of 7 to 12 carbon atoms, inclusive, wherein alkyl or aralkyl are substituted with zero to 3 halo atoms. Aromatic acyl groups include benzoyl and substituted benzoyl as represented by

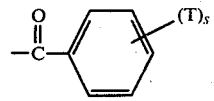

wherein T is alkyl of one to 4 carbon atoms, inclusive, phenylalkyl of 7 to 10 carbon atoms, inclusive, or nitro, and s is zero to 5, inclusive, provided that not more than two T's are other than alkyl, and that the total number of carbon atoms in the T's does not exceed 10 carbon atoms; mono-esterified phthaloyl as represented by

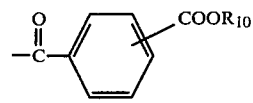

wherein $R_{10}$ is alkyl of one to 4 carbon atoms, inclusive; or naphthoyl and substituted naphthoyl as represented by

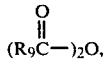

wherein T and s are as defined above.

In step (a) reduction of the formula-XVII lactone yields the formula-XXII diol. For this reduction, lithium aluminum hydride or diisobutylaluminum hydride are useful at 0°-35° C. Especially preferred is sodium bis(2-methoxyethoxy)aluminum hydride.

In step (b) the formula-XXIII diacylated compound is formed by acylation using methods known in the art or described herein. The two $R_8$ groups may be the same or different, for example one may be acetyl and the other pivaloyl. For the purpose herein it is preferred that the acyl group on the ring be somewhat more resistant to replacement by hydrolysis than the acyl group at the terminal position on the chain and one such preferred combination is with pivaloyl on the ring and acetyl on the chain. Acylation may be achieved with an acid anhydride such as acetic anhydride or with an acyl halide such as pivaloyl chloride. The reaction is done in the presence of a tertiary amine such as pyridine, triethylamine, and the like, and is carried out under a variety of conditions using procedures generally known in the art. Generally, mild conditions are employed, e.g. 20°-60° C., contacting the reactants in a liquid medium, e.g. excess pyridine or an inert solvent such as benzene, toluene or chloroform. The acylating agent is used either in stoichiometric amount or in excess.

Various carboxyacylating agents useful for this transformation are known in the art or readily obtainable by methods known in the art, and include carboxyacyl halides, preferably chlorides, bromides, or fluorides, i.e. $R_9C(O)Cl$, $R_9C(O)Br$, or $R_9C(O)F$, and carboxyacid anhydrides, $$(R_9C(O)-)_2O,$$

wherein $R_9$ is as defined above. Examples of acid anhydrides useful for this purpose are acetic anhydride, propionic anhydride, butyric anhydride, pentanoic anhydride, nonanoic anhydride, tridecanoic anhydride, stearic anhydride, (mono, di, or tri) chloroacetic anhydride, 3-chlorovaleric anhydride, 3-(2-bromoethyl)-4,8-dimethylnonanoic anhydride, cyclopropaneactic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, and phenoxyacetic anhydride. The choice of anhydride depends upon the identity of $R_9$ in the final acylated product, for example when $R_9$ is to be methyl, acetic anhydride is used; when $R_9$ is to be 2-chlorobutyl, 3-chlorovaleric anhydride is used.

When $R_9$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp 4 and 407 (1967) and references cited therein. Alternatively, the formula XXII diol is reacted with two equivalents of sodium hydride and then with excess ethyl formate.

In formula XXIII, $R_8$ may also represent benzoyl, substituted benzoyl, mono-esterified phthaloyl, naphthoyl or substituted naphthoyl. For introducing those blocking groups, methods known in the art are used. Thus, an aromatic acid, for example benzoic acid, is reacted with the formula-XXII compound in the presence of a dehydrating agent, e.g. sulfuric acid, zinc chloride, or phosphoryl chloride; or an anhydride of the aromatic acid, for example benzoic anhydride, is used.

As examples of reagents providing $R_8$ for the purposes of this invention, the following are available as acids, anhydrides, or acyl chlorides:

benzoyl;
substituted benzoyl, e.g.
(2-, 3-, or 4-)methylbenzoyl,
(2-, 3-, or 4-)ethylbenzoyl,
(2-, 3-, or 4-)isopropylbenzyl,
(2-, 3-, or 4-)tert-butylbenzoyl,
2,4-dimethylbenzoyl,
3,5-dimethylbenzoyl,
2-isopropyltoluyl,
2,4,6-trimethylbenzoyl,
pentamethylbenzoyl,
α-phenyl-(2-, 3-, or 4-)toluyl, 2-, 3-, or 4-4-phenethylbenzoyl,
2-, 3-, or 4-nitrobenzoyl,
(2,4-, 2,5-, or 3,5-)dinitrobenzoyl,
4,5-dimethyl-2-nitrobenzoyl,
2-nitro-6-phenethylbenzoyl,
3-nitro-2-phenethylbenzoyl;
mono-esterified phthaloyl, e.g.

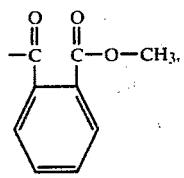

isophthaloyl, e.g.

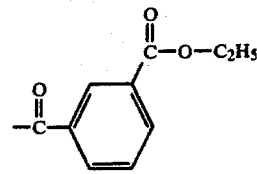

or terephthaloyl, e.g.

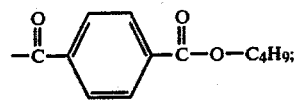

(1- or 2-)naphthoyl;
and substituted naphthoyl, e.g.
(2-, 3-, 4-, 5-, 6-, or 7-)-methyl-1-naphthoyl,
(2-, or 4-)ethyl-1-naphthoyl,
2-isopropyl-1-naphthoyl,
4,5-dimethyl-1-naphthoyl,
6-isopropyl-4-methyl-1-naphthoyl,
8-benzyl-1-naphthoyl,
8-benzyl-1-naphthoyl,
(3-, 4-, 5-, or 8-)-nitro-1-naphthoyl,
4,5-dinitro-1-naphthoyl,
(3-, 4-, 6-, 7-, or 8-)-methyl-1-naphthoyl,
4-ethyl-2-naphthoyl, and
(5- or 8-)-nitro-2-naphthoyl.

Continuing with Chart B, in step (c) the monoacylated compound of formula XXIV is obtained by selective hydrolysis. Generally a mild base such as potassium carbonate in methanol is sufficient to deacylate the terminal group on the chain. The hydrolysis of such esters is well known in the art and a wide choice of reagents and conditions is available to one skilled in the art.

In step (d) the formula-XXV acid is formed by oxidation, employing for example, the Jones reagent (J. Chem. Soc. 39, (1946)) at −40° to 25° C. in acetone.

In step (e) the formula-XXVI compound is obtained by oxidative decarboxylation, as described for Chart A above, using for example lead tetraacetate.

Finally in step (f) of Chart B the formula-X methylene compound is obtained on base hydrolysis of the monoacylated compound XXVI. Where $R_8$ is a hindered ester, stronger bases or more rigorous treatment are used than for step (c), for example with potassium carbonate at 50°–100° C. or with sodium or potassium hydroxide.

In Chart C, steps proceeding from methylene cyclopentanone derivative XI to phenylene-oxa products of formulas XLI and XLII are shown. In Chart C the terms A, Q, $Q_1$, $R_2$, $R_8$ and $R_{12}$ have the same meanings as for Charts A and B above; $R_{11}$ includes hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive.

In step (a), enone compound XI is subjected to conjugative addition with a lithium diaryl cuprate reactant prepared from

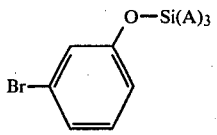

to yield compound XXVII. The term —Si(A)$_3$ is as defined above. The conditions for the reaction are similar to those described for Chart A above.

In step (b), compound XXVIII is obtained by reduction of the ketone, using methods known in the art or disclosed herein.

In step (c), the formula-XXIX acylated compound is formed by acylation of XXVIII, using methods known in the art or described herein.

In step (d) the terminal silyl group is removed to form compound XXX, using methods described above, for example hydrolysis with tetra-n-butylammonium fluoride.

In step (e) a Williamson synthesis is employed to obtain compound XXXI. The formula-XXX phenol is condensed with a haloacetate with the scope of Hal—CH$_2$—COOR$_{11}$ wherein Hal is chloro, bromo or iodo, and R$_{11}$ is as defined above for Chart C. Normally the reaction is done in the presence of a base such as n-butyllithium, phenyllithium, triphenylmethyllithium, sodium hydride, potassium hydride, potassium t-butoxide, sodium hydroxide, or potassium hydroxide.

In step (f) the formula-XXXII acid is obtained by base hydrolysis to replace R$_8$ and R$_{11}$ with hydrogen as is known in the art. Aqueous potassium hydroxide is useful at about 25°–100° C.

In step (g) ketone XXXIII is obtained by oxidation, using for example the Jones reagent.

In step (h) PGE-type product XLI is obtained by removing the R$_2$ blocking groups by mild acid hydrolysis as known in the art or described herein.

PGF-type products of formula XLII are obtained from intermediate XXXI by way of steps (i) and (j) of Chart C. In step (i) the R$_2$ blocking groups are removed, for example by the methods of step (h) to form compound XXXIV which is then converted to step (j) by base hydrolysis to compound XLII. The desired 9α compound is separated, if necessary, from the 9β epimer by methods known in the art, including silica gel chromatography.

Chart D shows a method for preparing inter-m-phenylene-PGF$_{1α}$ compounds by way of this invention. The formula-XIX starting materials have been described above as produced by step (i) of Chart A. In Chart D, the terms A, Q$_1$, R$_2$, R$_8$, and R$_{13}$ are as defined for Chart C above.

In step (a) the formula-XIX compound is acylated at the free hydroxyl at C-9, using methods described herein or known in the art.

In step (b) the formula-XXXVI compound is obtained by preferential hydrolysis to remove the silyl groups. Thereafter, in step (c) the terminal C-1 hydroxyl groups are oxidized to carboxyl groups using methods described above for step (k) of Chart A or methods known in the art.

In step (d) the C-9 acyl blocking groups R$_8$ are removed, as by base hydrolyses following the methods described above for step (f) of Chart C. Finally in step (e) the C-11 and C-15 blocking groups R$_2$ are removed by mild acid hydrolysis as known in the art, to yield the formula-XXXIX products.

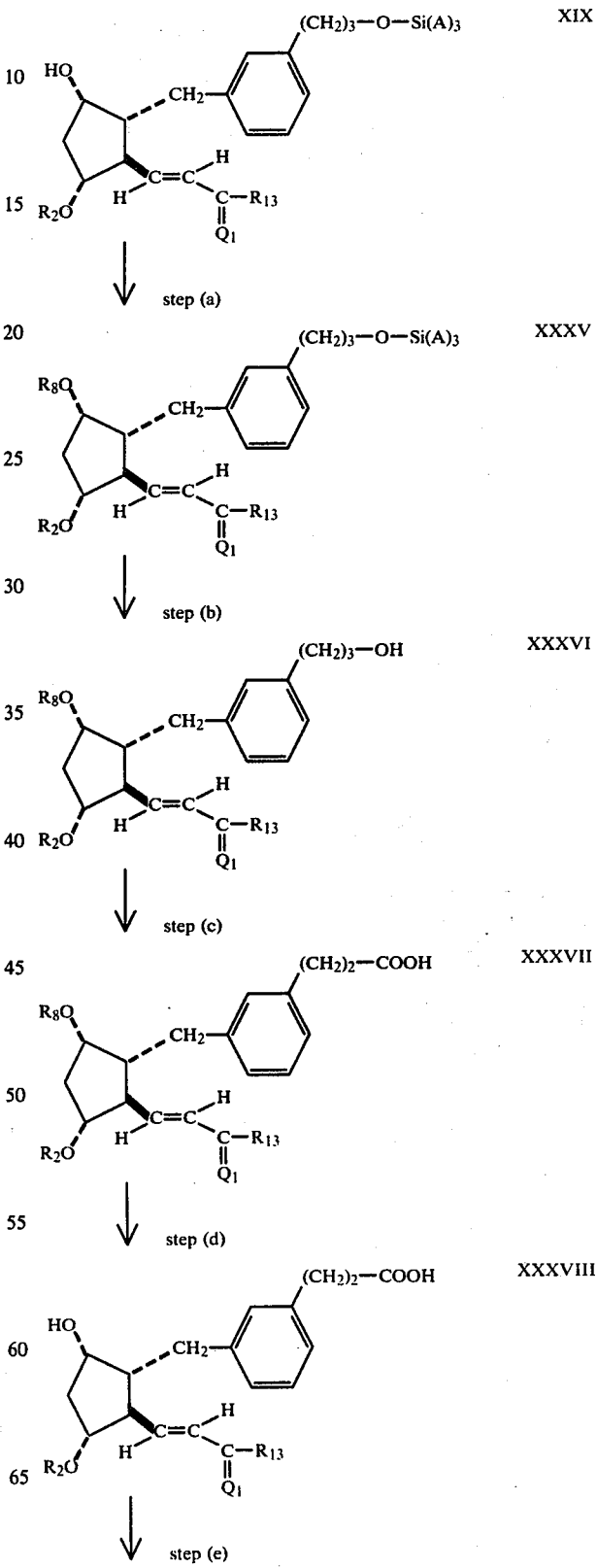

CHART D

-continued
CHART D

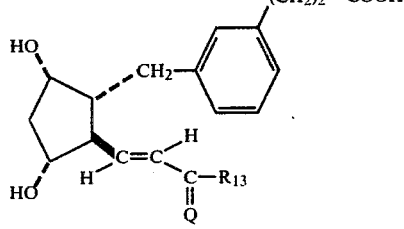

XXXIX

The novel intermediates of Charts A, B, C and D, including those compounds represented by formulas IX–XI and XIV–XXXVIII are frequently not isolated but used directly for a subsequent process step. When they are isolated, they are purified by methods known in the art, for example partition extraction, fractional crystallization, and, preferably, silica gel column chromatography.

The products represented by formulas XL, XLI, XLII, or XXXIX obtained from these intermediates retain the same stero configuration at C-15 as present in their respective starting materials of formula XII, XIII, XI, or XIX.

When an optically active intermediate or starting material is employed, subsequent steps yield optically active intermediates or products. When the racemic form of the intermediate or starting material is employed, the subsequent intermediates or products are obtained in their racemic form.

DESCRIPTION OF THE PREFERRED EMBODIMENTS

The invention can be more fully understood by the following examples and preparations:

All temperatures are in degrees centigrade.

Infrared absorption spectra are recorded on a Perkin-Elmer Model 421 or a Perkin-Elmer Infarcord infrared spectrophotometer. Except when specified otherwise, undiluted (neat) samples are used.

NMR spectra are recorded on a Varian A-60, A-60D, or T-60 spectrophotometer using deuterochloroform solutions with tetramethylsilane as an internal standard (downfield).

Mass spectra are recorded on a CEC Model 110B Double Focusing High Resolution Mass Spectrometer or an LKB Model 9000 Gass Chromatography-Mass Spectrometer (ionization voltage 70 ev.).

Circular dichroism curves are recorded on a Cary 60 recording spectropolarimeter.

Specific rotations are determined for solutions of a compound in the specified solvent with a Perkin-Elmer Model 141 Automatic Polarimeter.

"Brine", herein, refers to an aqueous saturated sodium chloride solution.

"Skellysolve-B" refers to mixed isomeric hexanes.

Silica gel chromatographic, as used herein, is understood to include elution, collection of fractions, and combination of those fractions shown by TLC (thin layer chromatography) to contain the desired product free of starting material and impurities.

The "A-IX system" for TLC is described by Hamberg and Samuelsson, J. Biol. Chem. 241, 257 (1966), and is based on ethyl acetate-acetic acid- 2,2,4-trimethylpentane-water (90:20:50:100).

PREPARATION 1

3-[3-(tert-Butyldimethylsilyloxy)-propyl]-phenyllithium Cuprate Reactant

I. There is first prepared 1-bromo-3-[3-(tert-butyldimethylsilyloxy)-propyl]benzene:

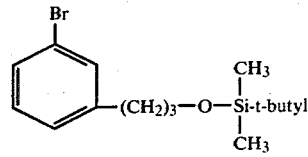

A solution of 3-(3-bromophenyl)-propan-1-ol (4.30 g.) in 15 ml. of dimethylformamide is treated with t-butyldimethylchlorosilane (3.62 g.) and imidazole (3.40 g.) at 25° C. for 3.5 hr. The mixture is diluted with brine and extracted with diethyl ether-Skellysolve B (1:1). The extracts are washed with 1 N. hydrochloric acid, aqueous sodium bicarbonate and brine, and dried over magnesium sulfate. Upon concentrating, 6 g. of oil is recovered, which, on distillation yields 5.68 g. of the silyl derivative, b. 84°–86° C./0.15 mm.

II. A solution of the above bromo compound (0.82 g.) in 20 ml. of diethyl ether is treated at −78° C. with tert-butyllithium (2.25 ml. of 1.20 M. solution in pentane), and stirred for 0.5 hr. The resulting solution of aryllithium compound is added to CuI.(n-C$_4$H$_9$)$_3$P complex prepared independently from copper (I) iodide (0.238 g.) and tri(n-butyl)phosphine (0.253 g.) in 20 ml. diethyl ether at 25° C. for 45 min. and cooled to −78° C. The resulting lithium cuprate reagent is then used directly in solution without isolation.

EXAMPLE 1

5α-(tert-Butyldimethylsilyloxy)-3α-hydroxy-2β-[(3'S)-3'-hydroxy-trans-1'-octenyl]-1α-cyclopentanacetic Acid, 3,3'-Bistetrahydropyranyl Ether (Formula XVI: Q$_1$ is

where THP is tetrahydropyran-2-yl, R$_2$ is THP, and Si(A)$_3$ is tert-butyldimethylsilyl).

I. Refer to Chart A, step (b). A solution of formula XIII lactone, specifically 3α,5α-dihydroxy-2β-[(3'S)-3'-hydroxy-trans-1'-octenyl]-1α-cyclopentan acetic acid, bistetrahydropyranyl ether (Corey et al., J. Am. Chem. Soc. 92, 397 (1970), 1.14 g.) in 10 ml. of methanol is treated with 10 ml. of 1 N. aqueous sodium hydroxide at about 25° C. for 2 hr. The reaction mixture is then concentrated to about one-half its volume, diluted with 50 ml. of water and saturated with sodium chloride. The pH is adjusted to about 5–6 with 1 M. aqueous potassium hydrogen sulfate and the mixture is extracted with ethyl acetate. The organic phase is washed with brine, dried over sodium sulfate, and concentrated to the formula-XIV compound, an oil.

II. Step (c). The resulting triol acid, bistetrahydropyranyl ether is taken up in 5 ml. of dimethylformamide and added to a solution of tert-butyldimethylchlorosilane (0.94 g.) and imidazole (0.88 g.) in 15 ml. of dimethylformamide. The mixture is stirred at 25° C. and after about 17 hr. additional reagents are added (0.47 g. of tert-butyldimethylsilyl chloride and 0.44 g. of imidazole) and stirring continued first at 25° C. for one hr. and then at 40° C. for 3 hr., the reaction then being complete as shown by TLC. The reaction mixture is cooled, diluted with brine, and extracted with 400 ml. of Skellysolve B-diethyl ether (1:1). The organic phase is separated, washed with 1 N. hydrochloric acid and brine, dried over sodium sulfate, and concentrated to yield the formula-XV compound.

III. Step (d). The residue from step (c) is dissolved in 175 ml. of a mixture of methanol-tetrahydrofuran-water (100:50:25) and treated with potassium carbonate (3.0 g.) at 25° C. for one hr. The reaction mixture is concentrated, diluted with 200 ml. of brine, adjusted to pH 4–5 with 1 M. aqueous potassium hydrogen sulfate, and extracted with ethyl acetate. The organic phase is washed with brine, dried over sodium sulfate, and concentrated to an oil containing the formula-XVI title compound. The product is subjected to silica gel chromatography, eluting with ethyl acetate (10–20%)-Skellysolve B, to yield the formula-XVI title compound, an oil, 1.36 g., having $R_f$ 0.14 (TLC on silica gel in ethyl acetate-Skellysolve B (1:3)), and NMR peaks at 0.3, 0.89, 0.7–2.8, 3.2–4.47, 4.68, 5.27–5.72, and 9.63 $\delta$; and IR absorption bands at 2980, 2890, 1735, 1710, 1460, 1253, 1198, 1183, 1130, 1110, 1074, 1019, 981, 870, 838 and 776 cm$^{-1}$.

EXAMPLE 2

1-(tert-Butyldimethylsilyoxy)-2-methylene4α-hydroxy-3β-[(3'S)-3'-hydroxy-trans-1'-octenyl[cyclopentane, 4,3'-Bistetrahydropyranyl Ether (Formula XVII: $Q_1$, $R_2$, and $Si(A)_3$ as defined in Example 1).

Refer to Chart A, step (e). A mixture of the formula-XVI silylated acid (Example 1, 2.20 g.) in 35 ml. of benzene is stirred with copper (II) acetate monohydrate (0.19 g.) and 1.16 ml. of pyridine until a homogeneous solution is produced. There is then added 5.03 g. of lead tetraacetate and the mixture stirred at about 25° C. in a dark place for 1.5 hr., with a slow stream of nitrogen passing through the mixture. With continued passage of nitrogen, the mixture is heated to 80° C. within 30 min. and kept at 80° C. for an additional 45 min. The course of the reaction is monitored with TLC. The reaction mixture is finally cooled to about 25° C., diluted with 300 ml. of brine, and extracted with ethyl acetate. The organic phase is washed with brine, dried over sodium sulfate, and concentrated to a residue containing the title compound, 2.25 g. The residue is subjected to silica gel chromatography, eluting with ethyl acetate (5–45%)-Skellysolve B, to yield the formula-XVII title compound, 0.80 g., having $R_f$ 0.64 (TLC on silica gel in ethyl acetate-Skellysolve B (1:3)); NMR peaks at 0.08, 0.92, 0.75–2.9, 2.9-4.5, 4.72, 4.93, 5.17, and 5.33–5.64 $\delta$; and IR absorption bands at 2960, 2895, 1460, 1345, 1251, 1199, 1120, 1075, 1065, 1034, 1020, 1002, 973, 900, 870, 838, 817, and 775 cm$^{-1}$.

EXAMPLE 3

2-Methylene-4α-hydroxy-3β-[(3'S)-3'-hydroxytrans-1'-octenyl]-cyclopentanol, 4,3'-Bistetrahydropyranyl Ether (Formula X: $Q_1$ and $R_2$ as defined in Example 1).

Refer to Chart A, step (f). A solution of the formula-XVII silylated compound (Example 2, 3.40 g.) in 40 ml. of tetrahydrofuran is treated with 15 ml. of 0.6 M. tetran-butylammonium fluoride and the mixture is stirred at about 25° C. for one hr. The resulting mixture is diluted with 300 ml. of brine and extracted wih diethyl ether. The organic phase is washed with brine, dried over magnesium sulfate, and concentrated. The residue (3.77 g.) is subjected to silica gel chromatography, eluting with ethyl acetate (10–50%)-Skellysolve B, to yield the formula-X title compound, now free of silyl groups, 1.94 g., a white solid, having $R_f$ 0.19 (TLC on silica gel in ethyl acetate-Skellysolve B (1:3)). An analytical sample, obtained on recrystallizing from Skellysolve B, has m.p. 83°–84.5° C.; NMR peaks at 0.88, 0.6–2.8, 3.0–4.5, 4.70, 5.02, and 5.20–5.62 $\delta$; and IR absorption bands at 3220, 3140, 1660, 1125, 1080, 1065, 1040, 1020, 1000, 970, and 910 cm$^{-1}$.

EXAMPLE 4

2-Methylene-4α-hydroxy-3β-[(3'S)-3'-hydroxy-trans-1'-octenyl cyclopentanone, 4,3'-Bistetrahydropyranyl Ether (Formula XI: $Q_1$ and $R_{13}$ as defined in Example 1).

Refer to Chart A, step (g). A solution of the formula-X allylic alcohol (Example 3, 0.41 g.) in 10 ml. of acetone is treated at −20° C. with 0.50 ml. of 2.67 M. Jones Reagent (Refer to Merck Index, Eighth Edition, page 1182 and references cited therein). The mixture is stirred at −20° to −15° C. for 30 min. and is then quenched with 0.25 ml. of isopropyl alcohol, stirring for an additional 10 min. The reaction mixture is then diluted with brine and extracted with diethyl ether. The organic phase is washed with aqueous sodium bicarbonate solution and brine, dried over sodium sulfate, and concentrated to the formula-XI title compound, 0.39 g., having IR absorption bands at 2980, 1735, 1647, 1200, 1129, 1112, 1076, 1035, 1020, and 978 cm$^{-1}$; and NMR peaks at 0.91, 0.8–3.1, 3.1–4.4, 4.68, 5.11, 5.47, 5.98 $\delta$; and having $R_f$ 0.44 (TLC on silica gel in ethyl acetate-Skellysolve B (1:3)).

EXAMPLE 5

2α-[7-(tert-Butyldimethylsilyloxy)-2,3,4-trinor-1,5-inter-m-phenylene-heptyl]-4α-hydroxy-3β-[(3'S)-3'-hydroxy-trans-1-octenyl]cyclopentanone, 4,3'-Bistetrahydropyranyl Ether (Formula XVIII: $Q_1$, $R_2$, and $Si(A)_3$ as defined in Example 1).

Refer to Chart A, step (h). A solution of the formula-XI enone compound of Example 4 (0.39 g.) in 4 ml. of diethyl ether at −78° C. is added to a solution of lithium cuprate reagent (Preparation 1) at −78° C. during 5–10 min. and thereafter stirred at −78° C. for 30 min. The reaction mixture is added, with rapid stirring, to a mixture of 50 ml. of 1 M. potassium hydrogen sulfate, 50 ml. of brine, and ice, diluted with brine, and extracted with diethyl ether. The organic extracts are washed with aqueous sodium bicarbonate and brine, dried over sodium sulfate, and concentrated to an oil, 1.50 g. The oil is subjected to silica gel chromatography, eluting with ethyl acetate (10–30%)-Skellysolve B, to yield the title compound, an oil, 0.49 g., having infrared spectral absorption bands at 2980, 2890, 1749, 1251, 1200, 1128, 1108, 1077, 1037, 1020, 974, 837, 776 cm$^{-1}$; NMR peaks at 0.004, 0.9, 0.9–3.05, 3.1–4.3, 3.62, 4.63, 5.43, and 6.68–7.37 $\delta$; $R_f$ 0.30 and 0.35 (TLC on silica gel plate in ethyl acetate-Skellysolve B (1:3)).

EXAMPLE 6

2α-[7-(tert-Butyldimethylsilyloxy)-2,3,4-trinor-1,5-inter-m-phenylene-heptyl]-4α-hydroxy-3β-[(3'S)-3'-hydroxy-trans-1-octenyl]cyclopentanol, 4,3'-Bistetrahydropyranyl Ether (Formula XIX: $Q_1$, $R_2$, and Si-(A)₃ as defined in EXample 1).

Refer to Chart A, step (i). A solution of the formula-XVIII ketone of Example 5 (0.49 g.) in 10 ml. of methanol is treated at 0° C. with sodium borohydride (0.060 g.) in 2 ml. of water, Tetrahydrofuran (5 ml.) is added and the mixture is stirred at 0° C. for one hr. The mixture is concentrated, diluted with brine, and extracted with ethyl acetate. The organic phase is washed with brine, dried over sodium sulfate, and concentrated to give the formula-XIX title compound and its C-9 epimer, an oil, 0.48 g., having $R_f$ 0.29 and 0.16 (TLC on silica gel plate in ethyl acetate-Skellysolve B (1:3)).

EXAMPLE 7

2α-(7-Hydroxy-2,3,4-trinor-1,5-inter-m-phenylene-heptyl)-4α-hydroxy-3β-[(3'S)-3'-hydroxytrans-1-octenyl]-cyclopentanol, 4,3'-Bistetrahydropyranl Ether (Formula XX: $Q_1$ and $R_2$ as defined in Example 1).

Refer to Chart A, step (j). A solution of the formula-XIX reduction product (Example 6, 0.48 g.) in 10 ml. of tetrahydrofuran is treated with tetra(n-butyl)ammonium fluoride (3 ml. of 0.5 M. solution at 25° C. for one hr., and then with an additional 1 ml. of tetra(n-butyl)ammonium fluoride solution for an additional hour). Brine is added and the mixture is extracted with ethyl acetate. The organic phase is washed with brine, dried over sodium sulfate, and concentrated to the formula-XX title compound and its C-9 epimer, an oil, 0.57 g., having $R_f$ 0.16 and 0.08 (TLC on silica gel plate in ethyl acetate-Skellysolve B (1:1)).

EXAMPLE 8

4,5,6-Trinor-3,7-inter-m-phenylene-PGE₁, 11,15-Bistetrahydropyranyl Ether. (Formula XXI: $Q_1$ and $R_2$ as defined in Example 1).

Refer to Chart A, step (k). A solution of the formula-XX compound of Example 7 (0.82 g.) in 30 ml. of acetone is treated at 20° C. with Jones reagent (2.0 ml. of 2.67 M. solution prepared from 2.1 g. chromium trioxide, 6 ml. of water and 1.7 ml. of concentrated sulfuric acid). After 1.6 hr. the reaction is complete and is quenched with 1.0 ml. of isopropyl alcohol, at 0° C. for 10 min. The mixture is diluted with brine and extracted with ethyl acetate. The organic phase is washed with brine, dried over sodium sulfate and concentrated to formula-XXI title compound, an oil, 0.86 g., having $R_f$=0.59 (TLC on silica gel plate in A-IX system).

EXAMPLE 9

4,5,6-Trinor-3,7-inter-m-phenylene-PGE₁ (Formula IV: Q is

).

Refer to Chart A, step (1). A solution of the formula-XXI compound of Example 8 (0.86 g.) in 15 ml. of acetic acid-water-tetrahydrofuran (20:10:3) is left at about 25° C. for 19 hr. The mixture is then diluted with 20 ml. of water and concentrated. The residue is taken up in 5 ml. of dichloromethane and subjected to silica gel chromatography, eluting with ethyl acetate (50–100%)-Skellysolve B, to yield the formula-IV title compound, 0.25 g., m. 67°–77° C., Rf 0.19 (TLC on silica gel in A-IX system). An analytical sample, obtained by recrystallizing from diethyl ether-Skellysolve B, has m.p. 65.9°–69.5° C.; NMR peaks at 0.95, 1.2–1.7, 1.9–3.2, 3.9–4.2, 5.3–5.7, 5.9–6.2, and 6.9–7.3 δ; $[α]_D$ −87° (c=0.8465 in chloroform); and mass spectral peaks (TMS derivative) at 604.3408, 589, 533, 514, 499, 443, 417, 389, 313, 279, and 199.

Following the procedures of Examples 1–9 but replacing the formula-XIII lactone starting material with the appropriate lactone wherein the terminal pentyl group of the octenyl side chain of 3α,5α-dihydroxy-2β-[(3'S)-3'-hydroxy-trans-1'-octenyl]-1α-cyclopentanacetic acid, bis-tetrahydropyranyl ether is replaced by each of the following groups, as known in the art or available by methods known in the art:

1-methylpentyl
1,1-dimethylpentyl
1-fluoropentyl
1,1-difluoropentyl
phenoxymethyl
(m-tolyloxy)methyl
(p-tolyoxy)methyl
(m-chlorophenoxy)methyl
(p-chlorophenoxy)methyl
(m-fluorophenoxy)methyl
(p-fluorophenoxy)methyl
(m-trichloromethylphenoxy)methyl
(p-trichloromethylphenoxy)methyl
(m-anisyloxy)methyl
(p-anisyloxy)methyl
1-phenoxyethyl
1-methyl-1-phenoxyethyl
benzyl
2-phenethyl
2-(m-tolyl)ethyl
2-(p-tolyl)ethyl
2-(m-chlorophenyl)ethyl
2-(p-chlorophenyl)ethyl
2-(m-fluorophenyl)ethyl
2-(p-fluorophenyl)ethyl
2-(m-trichloromethylphenyl)ethyl
2-(p-trichloromethylphenyl)ethyl
2-(m-anisyl)ethyl
2-(p-anisyl)ethyl
3-phenylpropyl
1-methyl-1-phenylethyl
1-methyl-2-phenylethyl
1,1-dimethyl-2-phenylethyl
1,1-dimethyl-3-phenylpropyl
α,α-difluorobenzyl
1-fluoro-2-phenylethyl
1,1-difluoro-2-phenylethyl and
1,1-difluoro-3-phenylpropyl there are obtained each of the corresponding formula-XL 4,5,6-trinor-3,7-inter-m-phenylene-PGE₁ analogs having one of the following structural features:
16-methyl-;
16,16-dimethyl-;
16-fluoro-;
16,16-difluoro-;
16-phenoxy-17,18,19,20-tetranor-;
16-(m-tolyloxy)-17,18,19,20-tetranor-;

16-(p-tolyloxy)-17,18,19,20-tetranor-;
16-(m-chlorophenoxy)-17,18,19,20-tetranor-;
16-(p-chlorophenoxy)-17,18,19,20-tetranor-;
16-(m-fluorophenoxy)-17,18,19,20-tetranor-;
16-(p-fluorophenoxy)-17,18,19,20-tetranor-;
16-(m-trichloromethylphenoxy)-17,18,19,20-tetranor-;
16-(p-trichloromethylphenoxy)-17,18,19,20-tetranor-;
16-(m-anisyloxy)-17,18,19,20-tetranor-;
16-(p-anisyloxy)-17,18,19,20-tetranor-;
16-phenoxy-18,19,20-trinor-;
16-methyl-16-phenoxy-18,19,20-trinor;
16-phenyl-17,18,19,20-tetranor-;
17-phenyl-18,19,20-trinor-;
17-(m-tolyl)-18,19,20-trinor-;
17-(p-tolyl)-18,19,20-trinor-;
17-(m-chlorophenyl)-18,19,20-trinor-;
17-(p-chlorophenyl)-18,19,20-trinor-;
17-(m-fluorophenyl)-18,19,20-trinor-;
17-(p-fluorophenyl)-18,19,20-trinor-;
17-(m-trichloromethylphenyl)-18,19,20-trinor-;
17-(p-trichloromethylphenyl)-18,19,20-trinor-;
17-(m-anisyl)-18,19,20-trinor-;
17-(p-anisyl)-18,19,20-trinor-;
18-phenyl-19,20-dinor-;
16-methyl-16-phenyl-18,19,20-trinor-;
16-methyl-17-phenyl-18,19,20-trinor-;
16,16-dimethyl-17-phenyl-18,19,20-trinor-;
16,16-dimethyl-18-phenyl-19,20-dinor-;
16,16-difluoro-16-phenyl-17,18,19,20-tetranor-;
16-fluoro-17-phenyl-18,19,20-trinor-;
16,16-difluoro-17-phenyl-18,19,20-trinor-; or
16,16-difluoro-18-phenyl-19,20-dinor-.

For example, starting with 3α,5α-dihydroxy-2β-[(3'S)-3,'-hydroxy-trans-1'-(5'-phenyl)pentenyl]-1α-cyclopentanacetic acid, bis tetranhydropyranyl ether there is obtained 4,5,6,18,19,20-hexanor-3,7-inter-m-phenylene-17-phenyl-PGE$_1$.

Likewise starting with the corresponding (3'R)-3'-hydroxy lactones, there are obtained the 15-epimeric products.

EXAMPLE 10

2-Methylene-4α-hydroxy-3β-[(3'S)-3'-hydroxy-trans-1'-octenyl]-cyclopentanol, 4,3'-Bistetrahydropyranyl Ether (Formula X: Q$_1$ and R$_2$ as defined in Example 1).

a. Refer to Chart B, step (a). A solution of formula-XIII lactone (Corey et al., J. Am. Chem. Soc. 92, 397 (1970), 4.29 g.) in 15 ml. of tetrahydrofuran is added dropwise to a stirred mixture of sodium bis(2-methoxyethoxy)aluminum hydride (70% solution in benzene, 4.3 g.) and 50 ml. of tetrahydrofuran at about 20° C. The mixture is stirred for an additional 2 hr. whereupon 100 ml. of 5% aqueous potassium hydroxide is added cautiously with stirring. The mixture is diluted with 200 ml. of diethyl ether and water (1:1). The organic phase is washed with 5% aqueous potassium hydroxide and brine, dried over sodium sulfate, and concentrated to yield the formula-XXII compound, an oil, 459 g., having infrared absorption bands at 3450, 2980, 2890, 1465, 1450, 1438, 1346, 1338, 1200, 1130, 1110, 1075, 1034, 1020,974, and 869 cm$^{-1}$.

b. Chart B, step (b). The diacylated formula-XXIII compound is next obtained from the diol product XXII of step (a) (4.59 g.) treated in 40 ml. of pyridine, and 10 ml. of acetic anhydride together with 0.1 g. of 4-dimethyl-aminopyridine as a catalyst. The reaction mixture is stired at about 25° C. for 16 hr., then diluted with brine and extracted with diethyl ether. The organic phase is washed with ice-cold 1 M. potassium acid sulfate and brine, dried over sodium sulfate, and concentrated to yield the formula-XXIII diacetate, and oil, 5.24 g.

c. Chart B, step (c). The product of step (b) (5.24 g.) is treated with potassium carbonate (0.14 g.) in 100 ml. methanol at about 40° C. for 1.25 hr. and finally at about 25° C. for 0.75 hr. The mixture is diluted with ice cold brine and 1 M. potassium acid sulfate to pH 2-3 and extracted with ethyl acetate. The organic phase is washed with brine, dried over sodium sulfate, and concentrated to an oil containing the formula-XXIV monoacetate, 4.56 g. The residue is subjected to silica gel chromatography, eluting with acetone (5-75%)-dichloromethane to obtain the formula-XXIV compound, an oil, 0.69 g., having R$_f$0.20 (TLC on silica gel in acetone-dichloromethane (15:85)); infrared absorption bands at 3530, 2970, 1740, 1242, 1130, 1111, 1073, 1032, 1020, 972 cm$^{-1}$; NMR peaks at 0.88, 0.7–3.0, 2.03, 3.15–4.3, 4.65, 5.13, 5.3–5.82 δ.

d. Chart b, step (d). The product of step (c) (0.69 g.) in 20 ml. of acetone is treated with 1.5 ml. of 2.67 M. Jones reagent added dropwise. The mixture is stirred at about 25° C. for 0.5 hr., diluted with brine, and extracted with diethyl ether. The ether extract is washed with brine, dried over sodium sulfate, and concentrated to an oil, 0.58 g. The residue is subjected to silica gel chromatography, eluting with ethyl acetate (10-50%)-Skellysolve B, to obtain the formula-XXV acid compound, 0.31 g., having R$_f$0.56 and 0.51 (TLC on silica gel in A-IX system); infrared absorption bands at 2970, 1745, 1240, 1032, and 1020 cm$^{-1}$; and NMR peaks at 0.89, 0.7–3.1, 2.05, 3.15–4.4, 4.65, 5.19, 5.46, 9.06 δ.

e. Chart B, step (e). The product of step (d) (0.31 g.) is treated in 10 ml. of benzene with 0.12 ml. of pyridine and 0.02 g. of copper (II) acetate monohydrate. After stirring in a dark place at about 25° C. for 45 min., the mixture is treated with 0.52 g. of lead tetraacetate. The mixture is stirred, first at about 25° C. for 45 min., then heated up to 80° C. in 15 min. and at 80° C. for 10 min. The mixture is cooled, diluted with brine, and extracted with ethyl acetate. The organic phase is washed with brine, dried over sodium sulfate, and concentrated to an oil, 0.37 g. The residue is subjected to silica gel chromatography, eluting with ethyl acetate (20-50%)-Skellysolve B, to yield the formula-XXVI methylene compound, 0.03 g., having R$_f$ 0.61 (TLC on silica gel in ethyl acetate-Skellysolve B(1:1); infrared absorption bands at 2970, 1740, 1235, 1035, and 1020 cm$^{-1}$; and NMR peaks at 0.90, 0.8–3.0, 2.07, 3.1–4.3, 4.67, 5.00, 5.27, and 5.43δ.

f. Chart B, step (f). Finally, the formula-X title compound is obtained by saponification of the remaining acyl group on the product of step (e) (0.03g.) treated in 2 ml. of methanol with 0.02 g. of potassium carbonate at about 25° C. for 45 min. The reaction mixture is diluted with brine and extracted with ethyl acetate. The extract is washed with brine, dried over sodium sulfate, and concentrated to yield the title compound, an oil, 0.22 g., having R$_f$ identical with that for the formula-X product of Example 3 above.

EXAMPLE 11

2-Methylene-4α-hydroxy-3β-[(3'S)-3'-hydroxy-trans-1'-octenyl]-cyclopentanol, 4,3'-Bistetrahydropyranyl Ether (Formula X: Q$_1$ and R$_2$ as defined in Example 1).

a. Refer to Chart B, step (b). The compound of formula-XXIII wherein $R_8$ in the terminal position of the chain is acetyl and $R_8$ on the ring is pivaloyl is prepared in two stages. The monoacetate is first prepared from compound XXII (Example 10-a, 5.56 g.), 50 ml. of pyridine, and 1.45 ml. of acetic anhydride, stirred at 0° C. for 2 hr., then allowed to warm to about 20° C. in 16 hr. The mixture is diluted with brine and extracted with ethyl acetate. The organic phase is washed with 1 N. hydrochloric acid to pH 2 in the washings, then with brine, dried, and concentrated to an oil, 5.88 g. The residue is subjected to silica gel chromatography, eluting with ethyl acetate (10–100%)-Skellysolve B, to yield the monoacetate, 3.41 g., having $R_f 0.29$ (TLC on silica gel in ethyl acetate-Skellysolve B (1:1); infrared absorption bands at 3530, 2975, 2890, 1745, 1239, 1133, 1077, 1032, 1020 and 981 cm$^{-1}$; and NMR peaks at 0.89, 0.9–2.8, 2.04, 3.1–4.38, 4.15, 4.72 and 5.53.

b. Continuing with Chart B, step (b). The product of step (a) above, having a terminal acetyl group on the chain (3.41 g.) is treated with 30 ml. of pyridine and 1.74 ml. of pivaloyl chloride at about 25° C. for 12 hr. The reaction is continued with additional 1.74 ml. of pivaloyl chloride at 40° C. for 3 hr. and at 23° C. for 16 hr. The reaction is quenched with 4 ml. of 85% lactic acid at 23° C. for one hr. The mixture is diluted with brine and extracted with ethyl acetate. The extract is washed with 1 N. hydrochloric acid-ice, sodium bicarbonate and brine, dried over sodium sulfate, and concentrated to the formula-XXIII compound having acetyl on the terminal position of the chain and pivaloyl on the ring. There is obtained 3.84 g., having $R_f 0.59$ (TLC on silica gel in ethyl acetate-Skellysolve B (1:1)); infrared absorption bands at 2980, 2890, 1745, 1755, 1280, 1160, 1032, and 1020 cm$^{-1}$; and NMR peaks at 0.87, 1.19, 1.98, 4.03, 4.67, 5.10, and 5.52$\delta$.

c. Chart B, step (c). The product of step (b) above (3.84 g.) is treated in 100 ml. of anhydrous methanol with 0.09 g. of potassium carbonate at about 25° C. for 0.5 hr. and at 40° C. for 1.5 hr. The reaction is continued with additional 0.09 g. of potassium carbonate at 40° C. for 2 hr. and at 24° C. for 16 hr. The mixture is concentrated and then diluted with brine and extracted with ethyl acetate. The organic phase is washed with brine, dried over sodium sulfate, and concentrated to yield the formula-XXIV product wherein $R_8$ is pivaloyl and $R_2$ is THP. There is obtained 3.42 g., having $R_f 0.34$ (TLC on silica gel in ethyl acetate-Skellysolve B (1:1)).

d. Chart B, step (d). The product of step (c) above (3.42 g.) is oxidized to the formula-XXV acid in 75 ml. of acetone at 0° C. with 6.54 ml. of 2.67 M. Jones reagent. In one hour the reaction is quenched with 2 ml. of isopropyl alcohol, stirring at 0° C. for 15 min. The mixture is concentrated, diluted with brine, and extracted with ethyl acetate. The extract is washed with water and brine, dried over sodium sulfate, and concentrated to an oil, 3.44 g. The residue is subjected to silica gel chromatography, eluting with ethyl acetate (20–40%)-Skellysolve B to yield the formula-XXV acid, an oil, 1.99 g., having $R_f 0.69$ and 0.74 (TLC on silica gel in A-IX system); and NMR peaks at 0.88, 1.18, 0.8–3.0, 3.1–4.3, 4.67, 5.16, 5.48, and 10.54$\delta$.

e. Chart B, step (e). The product of step (d) above is subjected to oxidative decarboxylation to form the formula-XXVI compound. The formula-XXV acid (1.99 g.) is treated in 35 ml. of benzene with 0.18 g. of copper (I) acetate monohydrate and 1.11 ml. of pyridine at about 25° C. for one hour. Lead tetraacetate (4.80 g.) is added and stirring continued in a dark place at about 25° C. for one hour, then to 80° C. in 10 min. and at 80° C. for 25 min. The mixture is cooled, diluted with brine, and extracted with ethyl acetate. The extract is washed with brine, dried over sodium sulfate, and concentrated to an oil, 2.11 g. The residue is subjected to silica gel chromatography, eluting with ethyl acetate (5–40%)-Skellysolve B, to yield the formula-XXVI methylene compound wherein $R_8$ is pivaloyl and $R_2$ is THP. There is obtained an oil, 0.15 g., having $R_f 0.43$ (TLC on silica gel in ethyl acetate-Skellysolve B (1:3)) and NMR peaks at 0.88, 0–8–2.9, 1.18, 3.0–4.4, 4.72, 5.00, 5.22, 5.45$\delta$.

f. Chart B, step (f). Finally, the formula-X title compound is obtained by saponification of the product of step (e) above, using excess sodium hydroxide in aqueous methanol at about 25° C. until shown by TLC to be converted. Thereafter the usual work-up with brine, extracting, washing, and concentrating yields the title compound having the same properties as the product of Example 3 above.

Following the procedures of Examples 1–4, 10 and 11 but replacing starting material XIII, i.e. $3\alpha,5\alpha$-dihydroxy-$2\beta$-[(3'S)-3'-hydroxy-trans-1'-octenyl]-$1\alpha$-cyclopentaneacetic acid, bistetrahydropyranyl ether with each of the formula-XIII lactones listed following Example 9, there are obtained the corresponding formula-XI enone compounds having the substituted side chains.

PREPARATION 2

3-(tert-Butyldimethylsilyloxy)-phenyl-lithium Cuprate Reactant

I. There is first prepared 1-bromo-3-(tert-butyldimethylsilyloxy)benzene:

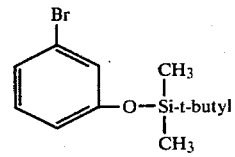

A solution of m-bromophenol (10.0 g.) in 40 ml. of dimethylformamide is treated with t-butyldimethylchlorosilane (17.42 g.) and imidazole (15.74 g.) at 23° C. for 16 hr. The mixture is diluted with brine and extracted with Skellysolve B-dichloromethane (3:1). The extracts are washed with brine, dried over sodium sulfate, and concentrated to an oil, 29.07 g. The oil is distilled to give the desired 1-bromo-3-(tert-butyldimethylsilyloxy)-benzene, 13.47 g., b.p. 66° C. (0.28 mm.).

II. A solution of the above bromo compound (4.40 g.) in 75 ml. of diethyl ether is treated at −78° C. with tert-butyllithium (12.14 ml. of 1.26 M. solution in pentane) and stirred for 40 min. The resulting solution of aryl-lithium compound is added to CuI.tri-n-butylphosphine complex prepared independently from copper (I) iodide (1.55 g.) and tri(n-butyl)phosphine (1.55 g.) in 50 ml. of diethyl ether at 25° C. for 45 min. The resulting lithium cuprate reagent is used directly without isolation.

EXAMPLE 12

$2\alpha$-[m-(tert-Butyldimethylsilyloxy)benzyl]-$4\alpha$-hydroxy-$3\beta$-[(3'S)-3'-hydroxy-trans-1-octenyl]cyclopentanone, 4,3'-Bistetrahydropyranyl Ether (Formula XXVII: $Q_1$, $R_2$, and $Si(A)_3$ as defined in Example 1).

Refer to Chart C, step (a). A solution of the formula-XI enone compound of Example 4 (2.49 g.) in 30 ml. of diethyl ether at −78° C. is added to a solution of lithium cuprate reagent (Preparation 2) at −78° C. during 15 min. with vigorous stirring and thereafter stirred for 30 min. The reaction mixture is added, with vigorous stirring to a mixture of 25 ml. of acetic acid in 225 ml. of diethyl ether at −78° C. The resulting solution is warmed to about 25° C., washed with brine and aqueous sodium bicarbonate and concentrated to an oil, 8.9 g. The oil is subjected to silica gel chromatography, eluting with ethyl acetate (10–40%)-Skellysolve B to yield the formula-XXVII title compound, an oil, 3.36 g., having NMR peaks at 0.18, 0.90, 0.98, 0.6–3.1, 3.2–4.4, 4.68, 5.50, and 6.52–7.42δ; infrared absorption bands at 2970, 2890, 1750, 1612, 1583, 1485, 1470, 1440, 1272, 1258, 1200, 1160, 1132, 1129, 1112, 1080, 1037, 1020, 976, and 784 cm$^{-1}$; and $R_f$ 0.29 and 0.34 (TLC on silica gel in ethyl acetate-Skellysolve B (1:3)).

EXAMPLE 13

2α-[3-(tert-Butyldimethylsilyloxy)benzyl]-4α-hydroxy-3β-[(3′S)-3′-hydroxy-trans-1-octenyl]cyclopentanol, 4,3′-Bistetrahydropyranyl Ether (Formula XXVIII: $Q_1$, $R_2$, and $Si(A)_3$ as defined in Example 1).

Refer to Chart C, step (b). A solution of the formula-XXVII ketone (Example 12, 3.2 g.) in 30 ml. of tetrahydrofuran is added dropwise to a mixture of lithium tri-(secbutylborohydride) (8.2 ml. of 1 M. solution in tetrahydrofuran) in 50 ml. of tetrahydrofuran at −78° C. and the mixture is stirred at −78° C. for 2 hr. The reaction mixture is quenched with 5 ml. of water and 2 ml. of 30% hydrogen peroxide and warmed to about 25° C. in one hr. The mixture is diluted with 500 ml. of brine and extracted with ethyl acetate. The extracts are washed with brine, dried over magnesium sulfate, and concentrated to yield the formula-XXVIII title compound, an oil, 3.54 g., having $R_f$ 0.30 (TLC on silica gel in ethyl acetate-Skellysolve B (1:3)).

EXAMPLE 14

3α-Hydroxy-5α-acetoxy-2β-[(3′S)-3′-hydroxytrans-1-octenyl]-1α-[3-(tert-butyldimethylsilyloxy)benzyl]-cyclopentane, 3,3′-Bistetrahydropyranyl Ether (Formula XXIX: $R_8$ is acetyl, and $Q_1$, $R_2$, and $Si(A)_3$ are as defined in Example 1).

Refer to Chart C, step (c). A solution of the formula-XXVIII hydroxy compound (Example 13, 3.54 g.) in 30 ml. of pyridine is treated at 0° C. with 7 ml. of acetic anhydride and 0.32 g. of 4-dimethylaminopyridine and stirred at 0° C. for one hr., finally at about 25° C. for 1.75 hr. The mixture is diluted with 400 ml. of brine, and extracted with ethyl acetate. The extracts are washed with brine, ice-cold 1 N. aqueous hydrochloric acid, saturated aqueous sodium bicarbonate, and brine, dried over sodium sulfate, and concentrated to the formula-XXIX title compound, an oil, 3.49 g., having $R_f$ 0.44 (TLC on silica gel in ethyl acetate-Skellysolve B (1:3)).

EXAMPLE 15

3α-Hydroxy-5α-acetoxy-2β-[(3′s)-3′-hydroxy-trans-1-octenyl-1α-(m-hydroxybenzyl)]cyclopentane, 3,3′-Bistetrahydropyranyl Ether (Formula XXX: $Q_1$, $R_2$, and $R_8$ are as defined in Example 14).

Refer to Chart C, step (d). A solution of the formula-XXIX silyl derivative (Example 14, 3.49 g.) in 15 ml. of tetrahydrofuran is treated with 14.4 ml. of 0.5 M. tetra-n-butylammonium fluoride in tetrahydrofuran at about 25° C. for 1.5 hr. The mixture is diluted with 200 ml. of brine and extracted with ethyl acetate. The extracts are washed with saturated aqueous sodium bicarbonate and brine, dried over sodium sulfate, and concentrated to an oil, 3.71 g. The oil is subjected to silica gel chromatography, eluting with ethyl acetate (25–55%)-Skellysolve B to yield the formula-XXX title compound, an oil, 2.25 g., having $R_f$ 0.11 (TLC on silica gel in ethyl acetate-Skellysolve B (1:3)); NMR peaks at 0.88, 2.06, 0.7–3.0, 3.10–4.37, 4.48–5.04, 5.56, 6.37–7.38, and 7.06 δ; and infrared absorption bands at 3390, 2960, 2885, 1737, 1715, 1590, 1446, 1368, 1237, 1100, 1152, 1128, 1073, 1020, and 972 cm$^{-1}$.

EXAMPLE 16

3-Oxa-4,5,6-trinor-3,7-inter-m-phenylene-PGF1α, 9-Acetate, 11,15-Bistetrahydropyranyl Ether, Methyl Ester (Formula XXXI: $R_{11}$ is methyl, and $Q_1$, $R_2$, and $R_8$ are as defined in Example 14).

Refer to Chart C, step (e). A mixture of the formula-XXX phenol (Example 15, 2.48 g.) in 30 ml. of 1,2-dimethoxyethane, methyl bromoacetate (1.39 g.) and 0.29 g. of 57% sodium hydride dispersion is stirred at about 25° C. for 2 hr. The mixture is then treated with 2 ml. of glacial acetic acid, diluted with brine, and extracted with ethyl acetate. The extract is washed with saturated aqueous sodium bicarbonate and brine, dried over magnesium sulfate, and concentrated to the formula-XXXI title compound, an oil. 3.20 g., having $R_f$ 0.48 in acetone-dichloromethane (15:85).

EXAMPLE 17

3-Oxa-4,5,6-trinor-3,7-inter-m-phenylene-PGF$_{1\alpha}$, 11,15-Bistetrahydropyranyl Ether (Formula XXXII: $Q_1$ and $R_2$ as defined in Example 1).

Refer to Chart C, step (f). A mixture of the formula-XXXI diester (Example 16, 2.45 g.) in 100 ml. of methanol and 30 ml. of 5% aqueous potassium hydroxide is heated at reflux for 5 hr., cooled, diluted with brine-ice, acidified to pH 3 with 1 M. aqueous potassium hydrogen sulfate, and extracted with ethyl acetate. The extracts are washed with brine, dried over sodium sulfate, and concentrated to formula-XXXII title compound, 2.46 g.

EXAMPLE 18

3-Oxa-4,5,6-trinor-3,7-inter-m-phenylene-PGE$_1$, 11,15-Bistetrahydropyranyl Ether (Formula XXXIII: $Q_1$ and $R_2$ as defined in Example 1) and 3-Oxa-4,5,6-trinor-3,7-inter-m-phenylene-PGE$_1$ (Formula VI: Q is

I. Refer to Chart C, step (g). A solution of the formula-XXXII PGF$_{1\alpha}$-type compound (Example 18, 2.46 g.) in 100 ml. of acetone is cooled to −20° C. and treated with 1.76 ml. of 2.67 M. Jones Reagent, stirring at −20° to −15° C. for 45 min. The reaction mixture is quenched with 3 ml. of isopropyl alcohol, stirred 10 min. more, diluted with brine, and extracted with ethyl acetate. The extracts are washed with brine, dried over sodium sulfate, and concentrated to the formula-XXXIII title compound, 2.17 g.

II. Step (h). A solution of the above bistetrahydropyranyl ether (2.17 g.) in 5 ml. of tetrahydrofuran, 30 ml. of acetic acid, and 15 ml. of water is stirred at 40° C. for 2.5 hr. The reaction mixture is then diluted with 300 ml. of water and freeze-dried to a semisolid residue containing the formula-VI title compound. The residue is subjected to silica gel chromatography, eluting with ethyl acetate (50–100%)-hexane to yield the formula-VI title compound, 0.77 g. Recrystallization from ethyl acetate-hexane gave colorless crystals, m.p. 134.5°–136.5° C.

EXAMPLE 19

3-Oxa-4,5,6-trinor-3,7-inter-m-phenylene-PGF$_{1\alpha}$, 9-Acetate, Methyl Ester (Formula XXXIV: Q is

$R_8$ is acetyl, and $R_{11}$ is methyl); and 3-Oxa-4,5,6-trinor-3,7-inter-m-phenylene-PGF$_{1\alpha}$(Formula VII: Q is

I. Refer to Chart C, step (i). A mixture of the formula-XXXI compound (Example 16, 0.75 g.) in 2 ml. of tetrahydrofuran, 10 ml. of acetic acid, and 5 ml. of water is stirred at 35° C. for 1.5 hr. and at 25° C. for 2 hr. The mixture is diluted with brine and extracted with ethyl acetate. The extract is washed with saturated aqueous sodium bicarbonate and brine, dried over sodium sulfate, and concentrated to the formula-XXXIV diester, an oil, 0.60 g.

II. Step (j). A solution of the above diester (0.60 g.) in 10 ml. of methanol is treated with 5 ml. of 5% aqueous potassium hydroxide at 25° C. for 12 hr. and then at reflux for 2 hr. The mixture is cooled, diluted with ice-cold brine, acidified to pH 3 with 1 M. aqueous potassium hydrogen sulfate, and extracted with ethyl acetate.

The extracts are washed with brine, dried over sodium sulfate, and concentrated to a residue, 0.44 g. The residue is subjected to silica gel chromatography, eluting with acetone (20–100%)-dichloromethane to yield the formula-VII title compound, 0.23 g., a solid. The product is recrystallized from ethyl acetate-hexane to yield colorless crystals, m.p. 100.1°–108.3° C., R$_f$ 0.06 (TLC on silica gel in A-IX system); NMR peaks at 0.88, 0.6–3.2, 3.97, 4.58, 4.64, 5.53, and 6.52–7.50 δ; infrared absorption bands at 3460, 3300, 2740, 2610, 2550, 1720, 1605, 1595, 1495, 1275, 1235, 1195, 1080, 1055, 1025, 975, 945 cm$^{-1}$; [α]$_D$ −18°(C. 0.7145 in ethanol); and mass spectral ions at 665.3512, 680, 609, 590, 575, 549, 519, 500, 443, 404, 353, 314, 237, and 217.

Following the procedures of Examples 12–19 but replacing the starting material XI, i.e. 2-methylene-4α-hydroxy-3β-[(3'S)-3'-hydroxy-trans-1'-octenyl]cyclopentanone, with each of the formula-XI enones following Example 11, there are obtained each of the corresponding 3-oxa-4,5,6-trinor-3,7-inter-m-phenylene-PGF$_{1\alpha}$-analogs having the structural features for the PGE$_1$ analogs obtained following Example 9.

EXAMPLE 20

2-Decarboxy-2-hydroxymethyl-4,5,6-trinor-3,7-inter-m-phenylene-PGF$_{1\alpha}$, 9-Acetate (Formula XXXVI: Q$_1$ is

where THP is tetrahydropyranyl, R$_8$ is acetyl, R$_2$ is THP, and R$_{13}$ is n-pentyl).

Refer to Chart D, steps (a) and (b). A solution of compound XIX (Example 6, 1.26 g.) in 15 ml. of pyridine is treated with 5 ml. of acetic anhydride and warmed to 45°–50° C. for 20 hr. The reaction mixture is diluted with brine and extracted with ethyl acetate. The combined extracts are washed with water, 1 N hydrochloric acid, saturated aqueous sodium bicarbonate, and brine, dried over sodium sulfate and concentrated to yield the formula-XXXV compound, an oil, having R$_f$ 0.37 (TLC on silica gel in 25% ethyl acetate in Skellysolve B).

A solution of the above formula-XXXV compound in 18 ml. of tetrahydrofuran is treated with 7 ml. of 0.5 M tetra-n-butylammonium fluoride in tetrahydrofuran. The reaction mixture is stirred at about 25° C. for 2.25 hr., diluted with brine and extracted with ethyl acetate. The combined extracts are washed with brine, dried over sodium sulfate, and concentrated. The residue is subjected to silica gel chromatography, eluting with ethyl acetate (30–60%)-Skellysolve B, to yield the title compound of formula XXXVI, 0.823 g., having R$_f$ 0.42 (TLC on silica gel in A-IX system.

EXAMPLE 21

4,5,6-Trinor-3,7-inter-m-phenylene-PGF$_{1\alpha}$(Formula XXXIX: Q is

and R$_{13}$ is n-pentyl).

Refer to Chart D steps (c), (d), and (e). A solution of alcohol XXXVI (Example 20, 0.84 g.) in 30 ml. of acetone is treated at −20° C. with 1 ml. of 2.67 M Jones Reagent. After one hr. the reaction is quenched with 0.5 ml. of isopropanol. The reaction mixture is diluted with brine and extracted with ethyl acetate. The combined extracts are washed with brine, dried over sodium sulfate, and concentrated to yield the formula-XXXVII acid, 0.89 g., having R$_f$ 0.58 (TLC on silica gel in A-IX system).

A solution of above acid XXXVII (0.89 g.) in 15 ml. of methanol is treated with 5 ml. of 5% aqueous potassium hydroxide and heated at reflux for 40 min. The reaction mixture is cooled to about 25° C., diluted with brine, acidified to pH 2–3 with ice-cold 1 M aqueous potassium hydrogen sulfate, and extracted with ethyl acetate. The combined extracts are washed with brine, dried over sodium sulfate, and concentrated to yield the formula-XXXVIII compound, 0.78 g., an oil having R$_f$ 0.42 (TLC on silica gel in A-IX system).

A solution of the above formula-XXXVIII compound (0.78 g.) in 15 ml. of acetic acid/water/tetrahydrofuran (20/10/3 by volume) is stirred at about 25° C. for 18 hr. The reaction mixture is then freeze-dried. The residue is subjected to silica gel chromatography, eluting with ethyl acetate (50–100%)-Skellysolve B followed by methanol (5%) in ethyl acetate, to give the formula XXXIX (V) title compound, 0.27 g., a solid having $R_f$ 0.12 (TLC on silica gel in A-IX system). An analytical sample, obtained by recrystallizing from ethyl acetate-Skellysolve B, has m.p. 109.8°–112.0° C.; NMR peaks at 0.88, 3.67–4.23, 5.02, 5.43–5.67, and 6.8–7.3 δ; and mass spectral peaks at 372, 354, 300, 191, 163, 121, 117, 93, 91, 79, 67, 43, and 41.

Following the procedures of Examples 20 and 21 but replacing starting material XIX, i.e. 2α-[7-(tert-Butyldimethylsilyloxy)-2,3,4-trinor-1,5-inter-m-phenyleneheptyl]-4α-hydroxy-3β-[(3'S)-3'-hydroxy-trans-1-octenyl]cyclo-pentanol, 4,3'-bistetrahydropyranyl ether with each of the formula-XIX intermediates obtained from the formula-XIII lactones listed following Example 9, there are obtained each of the corresponding formula-XXXIX 4,5,6-trinor-3,7-inter-m-phenylene-PGF$_{1\alpha}$ analog having the structural features listed for the PGE$_1$ analogs obtained following Example 9.

EXAMPLE 22

5α-(tert-Butyldimethylsiloxy)-3α-hydroxy-2β-[(3'S)-3'-hydroxy-4',4'-difluoro-trans-1'-octenyl]-1β-cyclopentane-acetic Acid, 3,3'-bis(tetrahydropyranyl ether) (Formula XVI: Q$_1$ is

R$_2$ is THP (tetrahydropyranyl), R$_{13}$ is

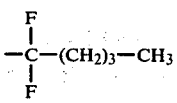

and

—Si(A)$_3$ is tert-butyldimethylsilyl).

1. Refer to Chart A, step (b). A solution of formula-XIII lactone, viz. 3α,5α-dihydroxy-2β-[(3'S)-3'-hydroxy-4',4'-difluoro-trans-1'-octenyl]-1α-cyclopentaneacetic acid, bis(tetrahydropyranyl ether) (U.S. Pat. No. 3,962,293; 17.10 g.) in 100 ml. is treated with 40 ml. of 1 N aqueous sodium hydroxide at about 25° C. for one hr. and then with additional 5 ml. for an additional 1.5 hr. The mixture is concentrated and diluted with 400 ml. of ice-cold brine and ice. There is added 0.5 M aqueous potassium hydrogen sulfate dropwise to pH 4–5 and the mixture is diluted with 300 ml. of brine and extracted with ethyl acetate. The organic phase is washed with brine, dried, and concentrated to the formula-XIV substituted acetic acid, a very viscous oil, having $R_f$ 0.42 (TLC on silica gel in A-IX).

II. Step (c). The above formula-XIV triol acid, bis(THP ether) is dissolved in 125 ml. of dimethylformamide and treated with t-butyl-dimethylsilyl chloride (21.97 g.) and imidazole (19.35 g.) at about 25° C. for about 16 hr. The mixture is diluted with brine and extracted with Skellysolve B. The organic phase is washed with water and brine, dried, and concentrated. The residue is the corresponding formula-XV compound, having $R_f$ 0.76 (TLC on silica gel in ethyl acetate-Skellysolve B (1:1)).

III. Step (d). The above formula-XV bis(silyl) compound in 200 ml. of methanol is treated with potassium carbonate (5.5 g.) added in 25 ml. of water at 25° C. for 2 hr. The mixture is concentrated to one-fourth volume, diluted with ice and ice-cold brine, and carefully acidified to pH 4–5 with 0.5 M. potassium hydrogen sulfate. The mixture is extracted with ethyl acetate. The organic phase is washed with brine, dried and concentrated to an oil, 24.8 g. The oil is chromatographed, eluting with ethyl acetate-Skellysolve B (1:3) to yield the formula-XVI title compound, an oil, 18.63 g., having $R_f$ 0.27 (TLC on silica gel in ethyl acetate-Skellysolve B (1:3)), NMR peaks at 8.58, 5.45–5.90, 3.25–5.00, 0.7–2.9, 0.90, and 0.05 δ, and infrared absorption at 1712, 1260, 1205, 1185, 1135, 1125, 1070, 1025, 975, 915, 870, 840, and 780 cm$^{-1}$.

EXAMPLE 23

1-(tert-Butyldimethylsilyloxy)-2-methylene-4α-hydroxy-3β-[(3'S)-3'-hydroxy-4',4'-difluoro-trans-1'-octenyl]-cyclopentane, 4,3'-bis(Tetrahydropyran-2-yl ether) (Formula XVII: Q$_1$, R$_2$, R$_{13}$, and Si(A)$_3$ as defined in Example 22).

Refer to Chart A, step (e). A mixture of 2.34 g. of the formula-XVI acid of Example 22, copper (II) acetate monohydrate (0.19 g.) and pyridine (1.16 ml.) in 35 ml. of benzene is stirred at about 25° C. until homogeneous. There is then added 5.03 g. of lead tetraacetate and the mixture stirred at about 25° C. in a dark place for one hr. under nitrogen. The mixture is heated to 80° C. within 20 min. and kept at 80° C. for an additional 20 min. The mixture is cooled and extracted with ethyl acetate. The organic phase is washed with water and brine and dried. This sequence is repeated using 16.29 g. of the formula-XVI acid, 1.32 g. of copper (II) acetate monohydrate, 8.08 ml. of pyridine and 250 ml. of benzene, followed by 35.01 g. of lead tetraacetate. The combined (dried) extracts are concentrated to an oil, 17.94 g. The oil is chromatographed, eluting with ethyl acetate (5–45%)-Skellysolve B, to yield the formula-XVII title compound, 5.71 g. and 9.62 g. of recovered formula-XVI starting material. The product has $R_f$ 0.59 (TLC on silica gel in ethyl acetate-Skellysolve B (1:3)), NMR peaks at 5.48–5.90, 5.16, 4.92, 3.0–4.9, 0.7–2.8, 0.91, and 0.08 δ, infrared absorption at 1665, 1255, 1200, 1120, 1075, 1065, 1035, 1020, 1005, 970, 905, 870, 840, and 775 cm$^{-1}$, and mass spectral lines at 501, 456, 417, 399, 315, and 85.

EXAMPLE 24

2-Methylene-4α-hydroxy-3β-[(3'S)-3'-hydroxy-4',4'-trans-1'-octenyl]-cyclopentanol, 4,3'-bis(Tetrahydropyran-2-yl ether) (Formula X: Q$_1$, R$_2$ and R$_{13}$ as defined in Example 22).

Refer to Chart A, step (f). A solution of the formula-XVII silylated compound (Example 23, 8.31 g.) in 50 ml. of tetrahydrofuran is treated at 0°–5° C. with 14.87 ml. of 1.5 M. tetra-n-butylammonium fluoride in tetrahydrofuran for 2 hr. The mixture is diluted with brine and extracted with ethyl acetate. The organic phase is washed with brine, dried, and concentrated to an oil, 9.85 g. The oil is chromatographed, eluting with ethyl acetate (35–45%)-Skellysolve B to yield the title compound, 6.29 g., a pale yellow solid. An analytical sample is obtained on crystallizing from hot Skellysolve B, m.p. 75.7°–77.5° C., having $R_f$ 0.09 (TLC on silica gel in ethyl acetate-Skellysolve B (1:3)), NMR peaks at 5.46–5.83, 5.37, 5.05, 3.1–4.9, 2.06, 0.8–2.8 and 0.92 δ, infrared absorption at 3220, 3140, 1665, 1200, 1130, 1120, 1080, 1065, 1040, 1025, 1010, 1000, 970, 905, and 870 cm$^{-1}$.

EXAMPLE 25

2-Methylene-4α-hydroxy-3β-[(3'S)-3'-hydroxy-4',4'-difluoro-trans-1-octenyl]-cyclopentanone, 4,3'-bis(Tetrahydropyran-2-yl ether) (Formula XI: $Q_1$, $R_2$, and $R_{13}$ as defined in Example 22).

Refer to Chart A, step (g). A solution of the formula-X cyclopentanol (Example 24, 99.75 mg.) in 3 ml. of acetone is treated at about −30° C. with 0.08 ml. of Jones reagent (1.5 equivalents). The mixture is stirred for 65 min. and is then quenched with 0.25 ml. of isopropanol, stirring for an additional 10 min. The reaction mixture is diluted with brine and extracted with ethyl acetate. The extract is washed with saturated aqueous sodium bicarbonate and brine, dried, and concentrated to an oil. A portion is chromatographed, eluting with ethyl acetate (15%)-Skellysolve B, to yield the title compound, 99.81 mg., having $R_f$ 0.31 and 0.35 for THP diastereomers (TLC on silica gel in ethyl acetate (25%)-Skellysolve B); NMR peaks at 5.75, 6.15, 5.28, 4.71, 3.16–4.50, 0.37–2.83, and 0.94 δ; and infrared absorption at 2950, 2880, 1750, 1635, 1375, 1195, 1115, 1070, 1030, 970, 905, 868, and 815 cm$^{-1}$.

Following the procedures of Examples 5–9, as represented in Chart A steps "h" through "l", but replacing the formula-XI cyclopentanone with the product of Example 25, there is obtained the corresponding 4,5,6-trinor-3,7-inter-m-phenylene-16,16-difluoro-PGE$_1$ product, a compound within the scope of those claimed in U.S. Pat. No. 4,084,058 and useful for the purposes disclosed therein.

Likewise following the procedures of Example 12–18, as represented in Chart C steps "a" through "h", but replacing the formula-XI cyclopentanone starting material with the product of Example 25, there is obtained the corresponding 3-oxa-4,5,6-trinor-3,7-inter-m-phenylene-16,16-difluoro-PGE$_1$ product, a compound within the scope of those claimed in U.S. Pat. No. 3,933,898 and useful for the purposes disclosed therein.

Another aspect of the present invention is the discovery that intermediates of formula X

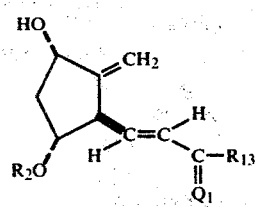

are surprisingly more stable than the corresponding compounds of formula XI

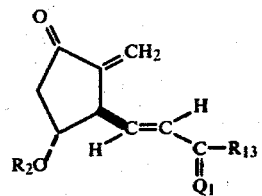

on storage at room temperature under nitrogen. The formula-XI cyclopentanones degraded within less than 3 days to the extent of 5 to 15% whereas the formula-X cyclopentanols were stable. This unexpected property indicates longer shelf-life for the cyclopentanols and accordingly that the cyclopentanols of formula X are unexpectedly more useful than the cyclopentanones for the purposes disclosed herein. The compounds wherein the ring hydroxy group of X is blocked with silyl, (A)$_3$Si—, or carboxyacyl

as defined herein, will also have greater stability than the cyclopentanones of formula XI.

I claim:
1. A compound of the formula

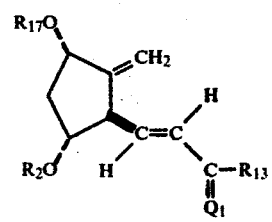

wherein $Q_1$ is

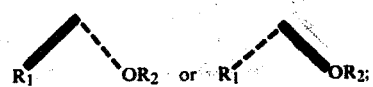

wherein $R_1$ is hydrogen or alkyl of one to 4 carbon atoms, inclusive; wherein $R_2$ is tetrahydropyranyl, tetrahydrofuranyl, or a group of the formula

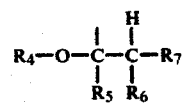

wherein $R_4$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_5$ and $R_6$ taken together are —(CH$_2$)$_b$—O—(CH$_2$)$_c$— wherein b is one, 2, or 3, and c is one, 2, or 3 with the proviso that b plus c is 2, 3, or 4, and wherein $R_7$ is hydrogen or phenyl; wherein $R_{13}$ is

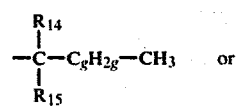

(1)

-continued $$\begin{array}{c} R_{14} \\ | \\ -C-Z- \\ | \\ R_{15} \end{array} \underset{}{\diagdown} (L)_p \quad (2)$$

wherein $C_gH_{2g}$ is alkylene of one to 9 carbon atoms, inclusive, with one to 5 carbon atoms, inclusive, in the chain between —$CR_{14}R_{15}$— and terminal methyl, wherein $R_{14}$ and $R_{15}$ are hydrogen, alkyl of one to 4 carbon atoms, inclusive, or fluoro, being the same or different, with the proviso that one of $R_{14}$ is fluoro only when the other is hydrogen or fluoro and the further proviso that neither $R_{14}$ nor $R_{15}$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_{14}R_{15}$— and the phenyl ring; and wherein L is alkyl of one to 4 carbon atoms, inclusive, fluoro, chloro, trifluoromethyl, or —$OR_{16}$— wherein $R_{16}$ is alkyl of one to 4 carbon atoms, inclusive, and p is zero, one, 2, or 3, with the proviso that not more than two L's are other than alkyl and when p is 2 or 3 the L's are either the same or different; and wherein $R_{17}$ is (1) silyl, —Si(A)$_3$ wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive, the A groups being the same or different; (2) carboxyacyl, represented by the formula $$\begin{array}{c} O \\ \| \\ R_9C- \end{array}$$

wherein $R_9$ is hydrogen, alkyl of one to 9 carbon atoms, inclusive, or aralkyl of 7 to 12 carbon atoms, inclusive, wherein alkyl or aralkyl are substituted with zero to 3 halo atoms; or (3) hydrogen.

2. A compound according to claim 1 wherein $R_{17}$ is silyl, —Si(A)$_3$, wherein A is as defined in claim 1.

3. A compound according to claim 2 wherein $R_{17}$ is tert-butyldimethyl-silyl and $Q_1$ is

[structure showing H and OR$_2$]

wherein $R_2$ is tetrahydropyran-2-yl.

4. A compound according to claim 3 wherein $R_{13}$ is n-pentyl, represented by the formula

[structure with t-C$_4$H$_9$—Si(CH$_3$)$_2$—O—, CH$_2$, THPO, C=C, nC$_5$H$_{11}$, OTHP]

wherein THP is tetrahydropyran-2-yl.

5. A compound according to claim 3 wherein $R_{13}$ is 1,1-difluoropentyl, represented by the formula

[structure with t-C$_4$H$_9$—Si(CH$_3$)$_2$—O—, CH$_2$, THPO, C=C, CF$_2$(CH$_2$)$_3$—CH$_3$, OTHP]

wherein THP is tetrahydropyran-2-yl.

6. A compound according to claim 1 wherein $R_{17}$ is pivaloyl.

7. A compound according to claim 6 wherein $Q_1$ is

[structure showing H and OR$_2$]

wherein $R_2$ is tetrahydropyran-2-yl.

8. A compound according to claim 7 wherein $R_{13}$ is n-pentyl, represented by the formula

[structure with t-C$_4$H$_9$—C(=O)—O—, CH$_2$, THPO, C=C, nC$_5$H$_{11}$, OTHP]

wherein THP is tetrahydropyran-2-yl.

9. A compound according to claim 1 wherein $R_{17}$ is acetyl.

10. A compound according to claim 9 wherein $Q_1$ is

[structure showing H and OR$_2$]

wherein $R_2$ is tetrahydropyran-2-yl, and $R_{13}$ is n-pentyl, represented by the formula

[structure with CH$_3$—C(=O)—O—, CH$_2$, THPO, C=C, nC$_5$H$_{11}$, OTHP]

wherein THP is tetrahydropyran-2-yl.

11. A compound according to claim 1 wherein $R_{17}$ is hydrogen.

12. A compound according to claim 11 wherein $Q_1$ is

[structure showing H and OR$_2$]

wherein $R_2$ is tetrahydropyran-2-yl.

13. A compound according to claim 12 wherein $R_{13}$ is n-pentyl, represented by the formula

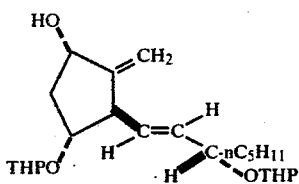

wherein THP is tetrahydropyran-2-yl.

14. A compound according to claim 12 wherein $R_{13}$ is 1,1-difluoropentyl, represented by the formula

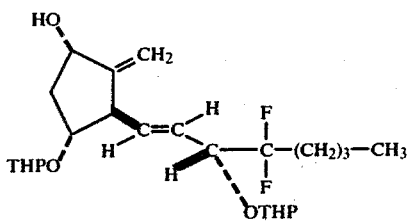

wherein THP is tetrahydropyran-2-yl.

15. A compound of the formula

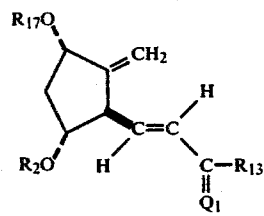

wherein $Q_1$ is

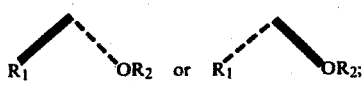

wherein $R_1$ is hydrogen or alkyl of one to 4 carbon atoms, inclusive; wherein $R_2$ is 1-ethoxyethyl or a group of the formula

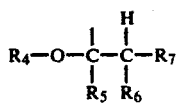

wherein $R_4$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_5$ and $R_6$ are the same or different, being hydrogen, alkyl of one to 4 carbon atoms, inclusive, phenyl or phenyl substituted with one, 2, or 3 alkyl of one to 4 carbon atoms, inclusive, or, when $R_5$ and $R_6$ are taken together, —(CH$_2$)$_a$— wherein a is 3, 4, or 5, and wherein $R_7$ is hydrogen or phenyl; wherein $R_{13}$ is

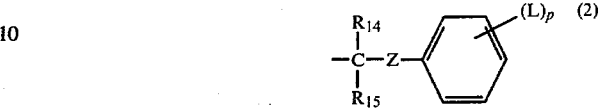

wherein $C_gH_{2g}$ is alkylene of one to 9 carbon atoms, inclusive, with one to 5 carbon atoms, inclusive, in the chain between —CR$_{14}$R$_{15}$— and terminal methyl, wherein $R_{14}$ and $R_{15}$ are hydrogen, alkyl of one to 4 carbon atoms, inclusive, or fluoro, being the same or different, with the proviso that one of $R_{14}$ and $R_{15}$ is fluoro only when the other is hydrogen or fluoro and the further proviso that neither $R_{14}$ nor $R_{15}$ is fluoro when Z is oxa (—O—); wherein Z represents an oxa atom (—O—) or $C_jH_{2j}$ is a valence bond or alkylene of one to 9 carbon atoms, inclusive, with one to 6 carbon atoms, inclusive between CR$_{14}$R$_{15}$— and the phenyl ring; and wherein L is alkyl of one to 4 carbon atoms, inclusive, fluoro, chloro, trifluoromethyl, or —OR$_{16}$— wherein $R_{16}$ is alkyl of one to 4 carbon atoms, inclusive, and p is zero, one, 2, or 3, with the proviso that not more than two L's are other than alkyl and when p is 2 or 3 the L's are either the same or different; and wherein $R_{17}$ is (1) silyl, —Si(A)$_3$ wherein A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive, the A groups being the same or different; (2) carboxyacyl, represented by the formula

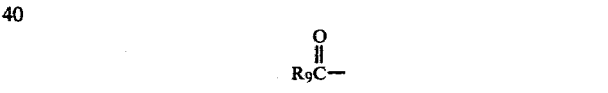

wherein $R_9$ is hydrogen, alkyl of one to 9 carbon atoms, inclusive, or aralkyl of 7 to 12 carbon atoms, inclusive, wherein alkyl or aralkyl are substituted with zero to 3 halo atoms; or (3) hydrogen.

16. A compound according to claim 15 wherein $R_{17}$ is silyl—Si(A)$_3$, wherein A is as defined in claim 15.

17. A compound according to claim 15 wherein $R_{17}$ is pivaloyl.

18. A compound according to claim 15 wherein $R_{17}$ is acetyl.

19. A compound according to claim 15 wherein $R_{17}$ is hydrogen.

* * * * *

UNITED STATES PATENT AND TRADEMARK OFFICE
CERTIFICATE OF CORRECTION

PATENT NO. : 4,181,798
DATED : 1 January 1980
INVENTOR(S) : D.R. Morton, Jr.

It is certified that error appears in the above—identified patent and that said Letters Patent is hereby corrected as shown below:

Column 39, line 13, "$R_{14}$ is fluoro" should read -- $R_{14}$ and $R_{15}$ is fluoro --.

Signed and Sealed this

Ninth Day of November 1982

[SEAL]

Attest:

GERALD J. MOSSINGHOFF

Attesting Officer    Commissioner of Patents and Trademarks